United States Patent [19]

Romero et al.

[11] Patent Number: 5,041,442

[45] Date of Patent: Aug. 20, 1991

[54] PYRROLO(1,2-A)PYRAZINES AS INHIBITORS OF GASTRIC ACID SECRETION

[75] Inventors: Ruth S. Romero, Estado de Mexico; Fidencio Franco, Mexico; Armando C. Castaneda, Jalisco, all of; Joseph M. Muchowski, Sunnyvale, Calif.

[73] Assignee: Syntex (U.S.A.) Inc., Palo Alto, Calif.

[21] Appl. No.: 560,528

[22] Filed: Jul. 31, 1990

[51] Int. Cl.$^5$ .................. A61K 31/495; C07D 487/04; C07D 207/333; C07D 207/34

[52] U.S. Cl. ................................. 514/249; 514/927; 544/349; 548/532; 548/539; 548/540; 548/537; 548/561; 548/562

[58] Field of Search .................. 544/349; 514/249

[56] References Cited

U.S. PATENT DOCUMENTS 4,450,164 5/1984 Bristol ........................... 546/121
4,507,294 3/1985 Bristol ........................... 544/117

OTHER PUBLICATIONS

Peresada *Khim.-Farm. Zh.* 1987, vol. 21, No. 9, pp. 1054–1059 (English Translation Provided).
Kaminski *J. Med. Chem.*, 1987, vol. 30, pp. 2031–2046.
*J. Med. Chem.*, 1987, vol. 30, pp. 2047–2051.

*Primary Examiner*—Mark L. Berch
*Attorney, Agent, or Firm*—Carol J. Roth; Derek P. Freyberg; Tom M. Moran

[57] ABSTRACT

This invention is directed to compounds of formula (I):

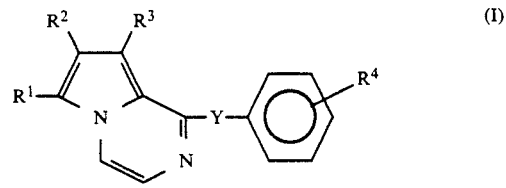

wherein
$R^1$ is thiocyano, —$CH_2CN$, —$NH_2$, —$NHR^5$, or —$CH_2OR^5$ where $R^5$ is lower alkyl;
$R^2$ is hydrogen, halo, lower alkyl, or lower alkylthio;
$R^3$ is hydrogen, halo, lower alkyl, lower alkylthio, or thiocyano;
$R^4$ is hydrogen, halo, lower alkyl, lower alkoxy, lower alkylthio, or lower alkylsulfonyl; and
Y is —O—$CH_2$—, —S—$CH_2$—, —CH=CH—, or —$(CH_2)_n$— where n is 0, 1, 2, 3 or 4;
or a pharmaceutically acceptable salt thereof. These compounds are useful in treating mammals having disease-states characterized by excessive gastric acid secretion.

33 Claims, No Drawings

PYRROLO(1,2-A)PYRAZINES AS INHIBITORS OF GASTRIC ACID SECRETION

BACKGROUND OF THE INVENTION

1. Field of the Invention

This invention relates to pyrrolo[1,2-a]pyrazine derivatives and their pharmaceutically acceptable salts, particularly those derivatives which are substituted at the 1-position by a phenylalkylene group and at the 6-position by an amino or a cyanomethyl group. These compounds inhibit gastric acid secretion and are therefore useful in treating mammals having disease-states characterized by excessive gastric acid secretion. This invention also relates to pharmaceutical compositions containing such compounds.

2. Related Disclosures

Certain substituted imidazo[1,2-a]pyrazine and imidazo[1,2-a]pyridine derivatives are known in the art as being useful in treating certain disease-states characterized by excessive gastric acid secretion, e.g., peptic ulcer disease. See, for example, U.S. Pat. No. 4,450,164 (Schering Corp.); U.S. Pat. No. 4,507,294 (Schering Corporation); *J. Med. Chem.* 1987, Vol. 30, pp. 2031-2046; and *J. Med. Chem.* 1987, Vol. 30, pp. 2047-2051.

Certain pyrrolo[1,2-a]pyrazines of the following formula:

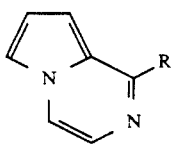

wherein R can be phenyl, 4-methoxyphenyl, 4-fluorophenyl, 4-chlorophenyl or phenylmethyl, are disclosed in *Khim. Farm. Zh.* 1987, Vol. 21, No. 9, pp. 1054-1059. These compounds are disclosed as having hypotensive activity.

SUMMARY OF THE INVENTION

In a first aspect, this invention provides a group of compounds represented by formula (I):

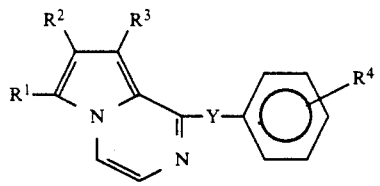

wherein
$R^1$ is thiocyano, —CH$_2$CN, —NH$_2$, —NHR$^5$, or —CH$_2$OR$^5$ where R$^5$ is lower alkyl;
$R^2$ is hydrogen, halo, lower alkyl, or lower alkylthio;
$R^3$ is hydrogen, halo, lower alkyl, lower alkylthio, or thiocyano;
$R^4$ is hydrogen, halo, lower alkyl, lower alkoxy, lower alkylthio, or lower alkylsulfonyl; and
Y is —O—CH$_2$—, —S—CH$_2$—, —CH=CH—, or —(CH$_2$)$_n$— where n is 0, 1, 2, 3 or 4;
or a pharmaceutically acceptable salt thereof.

In another aspect, this invention provides a group of compounds represented by formula (LL):

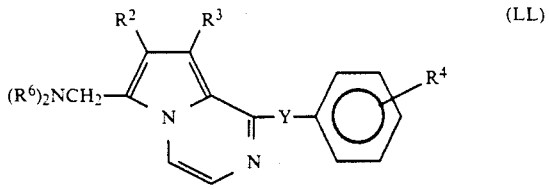

wherein
$R^2$ is hydrogen, halo, lower alkyl, or lower alkylthio;
$R^3$ is hydrogen, halo, lower alkyl, lower alkylthio, or thiocyano;
$R^4$ is hydrogen, halo, lower alkyl, lower alkoxy, lower alkylthio, or lower alkylsulfonyl;
$R^6$ is lower alkyl; and
Y is —O—CH$_2$—, —S—CH$_2$—, —CH=CH—, or —(CH$_2$)$_n$— where n is 0, 1, 2, 3 or 4;
or a pharmaceutically acceptable salt thereof. These compounds are useful as intermediates for the synthesis of the compounds of formula (I) wherein R$^1$ is —CH$_2$CN and —CH$_2$OR$^5$.

In another aspect, this invention provides compositions useful in the treatment of a mammal having a disease-state characterized by excessive gastric acid secretion, which composition comprises a therapeutically effective amount of a compound of formula (I) as described above, or a pharmaceutically acceptable salt thereof, and a pharmaceutically acceptable excipient.

In another aspect, this invention provides a method for treating a mammal having a disease-state characterized by excessive gastric acid secretion, which method comprises administering to a mammal in need thereof a therapeutically effective amount of a compound of formula (I) or a pharmaceutically acceptable salt thereof.

DETAILED DESCRIPTION OF THE INVENTION

Definitions

As used in the specification and appended claims, unless specified to the contrary, the following terms having the meaning indicated:

The term "lower alkyl" refers to a straight or branched chain monovalent radical consisting solely of carbon and hydrogen, containing no unsaturation and having from one to four carbon atoms, e.g., methyl, ethyl, n-propyl, 1-methylethyl, n-butyl, 1-methylpropyl, and the like.

The term "halo" refers to a halogen radical, i.e., fluoro, chloro, bromo or iodo.

The term "lower alkylthio" refers to a radical of the formula —SR$_a$ where R$_a$ is lower alkyl as defined above, e.g., methylthio, ethylthio, n-propylthio, n-butylthio, 2-methylpropylthio, and the like.

The term "lower alkylsulfonyl" refers to a radical of the formula —S(O)$_2$R$_a$ where R$_a$ is lower alkyl as defined above, e.g., methylsulfonyl, ethylsulfonyl, n-propylsulfonyl, n-butylsulfonyl, n-pentylsulfonyl, 2-methylpropylsulfonyl, and the like.

The term "lower alkyl halide" refers to a lower alkyl radical as defined above that is substituted by a halogen atom, e.g., methyl iodide, methyl bromide, methyl chloride, ethyl iodide, ethyl chloride, n-propyl bromide, and the like.

The term "lower alkyldisulfide" refers to a compound of the formula R$_a$—S—S—R$_a$ where R$_a$ is lower alkyl as defined above, e.g., methyldisulfide, ethyldisulfide, n-propyldisulfide, n-butyldisulfide, and the like.

The term "ω-phenylalkyl halide" refers to a compound of the formula X—(CH$_2$)$_n$—R$_b$ where X is halo as defined above, n is 1 to 4, and R$_b$ is phenyl optionally substituted with halo, lower alkyl, lower alkoxy, lower alkylthio, or lower alkylsulfonyl, e.g., benzyl bromide, 4-methylbenzyl bromide, 4-methylthiobenzyl chloride, 2-methoxybenzyl chloride, 2-phenyl-1-chloroethane, 2-phenyl-1-bromoethane, 2-phenyl-1-iodoethane, 3-(4-methyl)phenyl-1-chloropropane, 3-phenyl-1-bromopropane 3-(4-bromo)phenyl-1-chloropropane, 4-phenyl-1-bromobutane, 4-(2-methoxy)phenyl-1-bromobutane, and the like.

The term "ω-phenylalkanoyl halide" refers to a compound of the formula X—C(O)—(CH$_2$)$_n$—R$_b$ where X is halo as defined above, n is 0 to 4, and R$_b$ is phenyl optionally substituted with halo, lower alkyl, lower alkoxy, lower alkylthio, or lower alkylsulfonyl, e.g., benzoyl chloride, 4-methoxybenzoyl chloride, 4-methylthiobenzoyl chloride, benzoyl bromide, 2-phenylethanoyl chloride, 2-(4-methyl)phenylethanoyl bromide, 2-phenylethanoyl iodide, 3-(3-bromo)phenylpropanoyl chloride, 3-phenylpropanoyl bromide, 4-phenylbutanoyl chloride, and the like.

The term "thiocyano" refers to the radical —SCN.

The term "pharmaceutically acceptable salt" refers to those salts which retain the biological effectiveness and properties of the free bases and which are not biologically or otherwise undesirable. These salts may be prepared from either inorganic acids such as hydrochloric acid, hydrobromic acid, sulfuric acid, nitric acid, phosphoric acid, and the like; or organic acids such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

The term "mammal" includes humans and all domestic and wild mammals, including, without limitation, horses, swine, goats, dogs, cats, and the like.

The term "therapeutically effective amount" refers to that amount of a compound of formula (I) which, when administered to a mammal in need thereof, is sufficient to effect treatment, as defined below, for disease states characterized by excessive gastric acid secretion, for example, peptic ulcer disease. What amount constitutes a "therapeutically effective amount" will vary depending on the compound, the disease-state and its severity, and the mammal to be treated, but may be determined routinely by one of ordinary skill in the art having regard to his own knowledge and to this disclosure.

The term "treating or treatment" as used herein covers the treatment of a disease-state in a mammal, particularly in a human, which disease-state is characterized by excessive gastric acid secretion, for example, peptic ulcer disease, and includes:

(i) preventing the disease-state from occurring in a mammal, in particular, when such mammal is predisposed to the disease-state but has not yet been diagnosed as having it;

(ii) inhibiting the disease-state, i.e., arresting its development; or (iii) relieving the disease-state, i.e., causing regression of the disease-state.

The nomenclature used herein is basically a modified form of I.U.P.A.C. nomenclature wherein compounds of the invention are named as derivatives of pyrrolo[1,2-a]pyrazines. The positions in the compounds are indicated as follows:

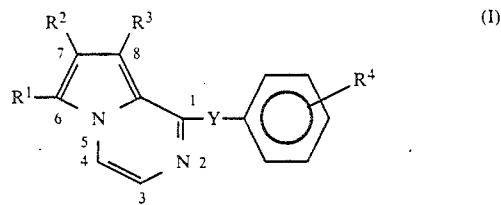

Thus, the following compound, a compound of formula (I), wherein R$^1$ is —CH$_2$CN, R$^2$ is hydrogen, R$^3$ is n-propylthio, R$^4$ is hydrogen and Y is —CH$_2$CH$_2$—, is named 1-(2-phenylethyl)-6-cyanomethyl-8-n-propylthiopyrrolo[1,2-a]pyrazine:

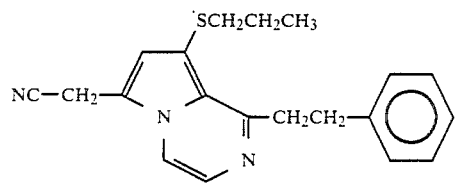

Utility and Administration

A. Utility

The compounds of formula (I), including the pharmaceutically acceptable salts thereof, and the compositions containing them, inhibit gastric acid secretion and are therefore useful in treating disease states characterized by excessive gastric acid secretion, e.g., peptic ulcer disease. In particular, these compounds inhibit gastric acid secretion in mammals by inhibiting the activity of the enzyme, H$^+$/K$^+$-ATPase, (the proton pump). H$^+$/K$^+$-ATPase is located in the secretory membranes of the parietal cell of the gastric mucosa and, when activated, is directly responsible for the secretion of hydrogen ions into the gastric lumen. Accordingly, by inhibiting this enzyme, the compounds of formula (I) inhibit gastric acid secretion. The compounds of formula (I) may therefore be used prophylactically (e.g., to prevent excessive gastric acid secretion) and/or therapeutically (e.g., to inhibit or relieve excessive gastric acid secretion).

B. Testing

The inhibitory effect on the activation of H$^+$/K$^+$-ATPase of the compounds of formula (I) can be determined by a variety of assays.

In vitro activity is determined by procedures utilizing the assay described in Serrato, C., et al., *Proc. West. Pharmacol. Soc.*, 1989, Vol. 32, pp. 249–253, or a modification thereof.

In vivo activity is determined by procedures utilizing the assays described in Shay, H., et al., *Gastroenterology* 1945, Vol. 5, pages 43–61, or modifications thereof, or the methods described in Serrato, C., et al., supra, or modifications thereof.

C. General Administration

Administration of the compounds of formula (I), in pure form or in an appropriate pharmaceutical composition, can be carried out via any of the accepted modes of administration of agents for serving similar utilities. Thus, administration can be, for example, orally, nasally, parenterally, rectally or topically, in the form of solid, semi-solid, lyophilized powder, or liquid dosage forms, such as for example, tablets, suppositories, pills, capsules, powders, solutions, suspensions, emulsions, creams, lotions, aerosols, ointments or the like, preferably in unit dosage forms suitable for simple administration of precise dosages. The compositions will include a conventional pharmaceutical carrier or excipient and an active compound of formula (I) and, in addition, may include other medicinal agents, pharmaceutical agents, carriers, adjuvants, etc.

Generally, depending on the intended mode of administration, the pharmaceutically acceptable compositions will contain about 1% to about 99% by weight of the pharmaceutically active compound of formula (I) and 99% to 1% by weight of a suitable pharmaceutical excipient. Preferably, the composition will be about 5% to 75% by weight of a compound of formula (I), with the rest being suitable pharmaceutical excipients.

The preferred manner of administration is oral using a convenient daily dosage regimen which can be adjusted according to the degree of gastric acid secretion to be inhibited. For such oral administration, a pharmaceutically acceptable composition containing a compound of formula (I) is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like.

Preferably such compositions will take the form of a pill or tablet and therefore will also contain a diluent such as lactose, sucrose, dicalcium phosphate, and the like; a disintegrant such as starch or derivatives thereof; a lubricant such as magnesium stearate and the like; and a binder such as a starch, gum acacia, polyvinylpyrrolidone, gelatin, cellulose and derivatives thereof, and the like.

The compounds of formula (I) may also be formulated into a suppository using, for example, about 0.5% to about 50% active ingredient disposed in a carrier that slowly dissolves within the body, e.g., polyoxyethylene glycols and polyethylene glycols (PEG) [e.g., PEG 1000 (96%) and PEG 4000 (4%)].

Liquid pharmaceutically administrable compositions can, for example, be prepared by dissolving, dispersing, etc., a compound of formula (I) (about 0.5% to about 20%), and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's Pharmaceutical Sciences, 16th Ed., (Mack Publishing Company, Easton, Pa., 1980). The composition to be administered will, in any event, contain an therapeutically effective amount of the compound of formula (I) for relief of excessive gastric acid secretion when administered in accordance with the teachings of this invention.

Generally, the compounds of formula (I) are administered in a therapeutically effective amount which will vary depending on the individual and the disease state characterized by excessive gastric acid secretion which is being treated. Typically, a therapeutically effective daily dose is from about 0.02 to 100 mg/kg of body weight per day of a compound of formula (I), for example, from about 0.4 to 30 mg/kg of body weight per day, and most preferably about 10 mg/kg/day. Thus, for administration to a 70 kg person, the dosage range would be from about 1.4 mg to 7.0 g per day, preferably from about 28 mg to 2.1 g per day, most preferably about 700 mg/kg/day.

Preferred Embodiments

One aspect of the invention is the group of compounds represented by formula (I):

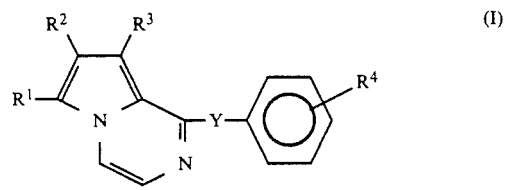

wherein
$R^1$ is thiocyano, —CH$_2$CN, —NH$_2$, —NHR$^5$, or —CH$_2$OR$^5$ where $R^5$ is lower alkyl;
$R^2$ is hydrogen, halo, lower alkyl, or lower alkylthio;
$R^3$ is hydrogen, halo, lower alkyl, lower alkylthio, or thiocyano;
$R^4$ is hydrogen, halo, lower alkyl, lower alkoxy, lower alkylthio, or lower alkylsulfonyl; and
Y is —O—CH$_2$—, —S—CH$_2$—, —CH=CH—, or —(CH$_2$)$_n$— where n is 0, 1, 2, 3 or 4;
or a pharmaceutically acceptable salt thereof. Within this group of compounds certain subgroups are preferred. These subgroups and their relative degrees of preference are described below.

A preferred subgroup of compounds is that subgroup wherein $R^1$ is —CH$_2$CN or —NH$_2$.

Another preferred subgroup of compounds is that subgroup wherein $R^2$ is hydrogen, halo or lower alkyl. Within this subgroup a preferred class of compounds is that class wherein $R^2$ is hydrogen, bromo or methyl.

Another preferred subgroup of compounds is that subgroup wherein $R^4$ is in the 4-position and is hydrogen, lower alkyl or halo. Within this subgroup a preferred class of compounds is that class wherein $R^4$ is hydrogen, methyl or chloro.

Another preferred subgroup of compounds is that subgroup wherein Y is —(CH$_2$)$_n$— where n is 0 or 2.

Preferred compounds of formula (I) are those where $R^3$ is as defined in the Summary of Invention, Y is —(CH$_2$)$_n$— where n is 0 or 2, and at least one of $R^1$, $R^2$ and $R^4$ is preferred as described above. More preferred are those compounds where more than one of $R^1$, $R^2$ or $R^4$ is preferred as described above. Even more preferred are those compounds where each $R^1$, $R^2$ and $R^4$ is preferred as described above. Presently the most preferred compounds of this invention are:

1-(2-phenylethyl)-6-amino-8-ethylpyrrolo[1,2-a]pyrazine;

1-(2-phenylethyl)-6-amino-7-methyl-8-ethylpyrrolo[1,2-a]pyrazine;

1-(2-phenylethyl)-6-amino-7-methyl-8-bromopyrrolo[1,2-a]pyrazine;

1-(2-phenylethyl)-6-amino-8-methylthiopyrrolo[1,2-a]pyrazine;

1-(2-phenylethyl)-6-cyanomethyl-8-ethylthiopyrrolo[1,2-a]pyrazine;

1-(2-phenylethyl)-6-cyanomethyl-8-n-propylthiopyrrolo[1,2-a]pyrazine;

1-(2-phenylethyl)-6-cyanomethyl-8-n-butylthiopyrrolo[1,2-a]pyrazine;

1-(2-(4-methylphenyl)ethyl)-6-cyanomethyl-8-thiocyanopyrrolo[1,2-a]pyrazine;

1-(2-phenylethyl)-6-cyanomethyl-7-methyl-8-ethylpyrrolo[1,2-a]pyrazine;

1-(2-phenylethyl)-6-cyanomethyl-7-bromo-8-thiocyanopyrrolo[1,2-a]pyrazine; and 1-(2-phenylethyl)-6-cyanomethyl-7,8-dichloropyrrolo[1,2-a]pyrazine.

Processes for Preparing Compounds of Formula (I)

A. Preparation of the Compounds of Formula (Ia)

Compounds of formula (Ia) are compounds of formula (I) wherein $R^1$ is thiocyano, —$NH_2$, or $NHR^5$; $R^2$, $R^3$ and $R^4$ are as defined above in the Summary of the Invention; and Y is —$(CH_2)_n$— where n is 0, 1 or 2. They are synthesized as shown in the following Reaction Scheme 1 wherein X is bromo or chloro; $R^7$ is hydrogen, bromo or chloro; and $R^8$ is hydrogen or bromo:

REACTION SCHEME 1

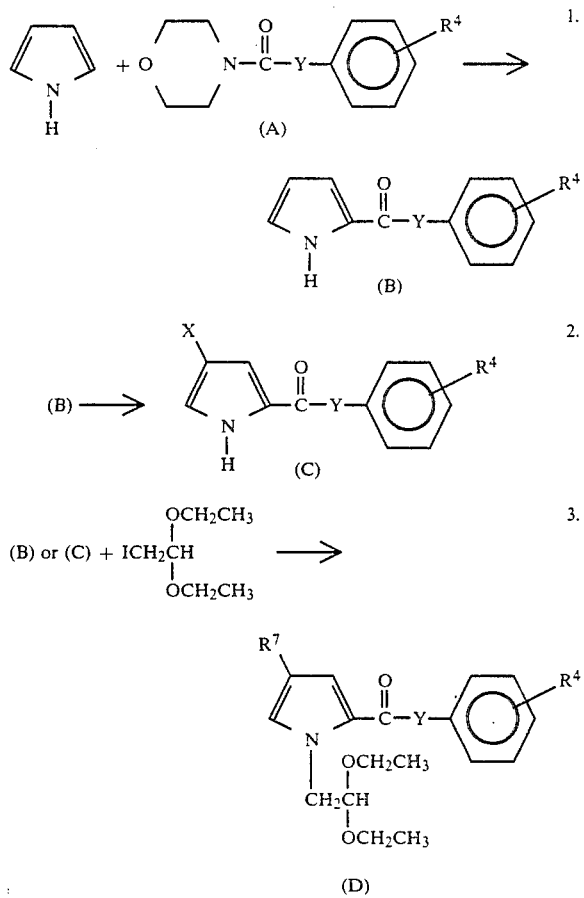

-continued
REACTION SCHEME 1

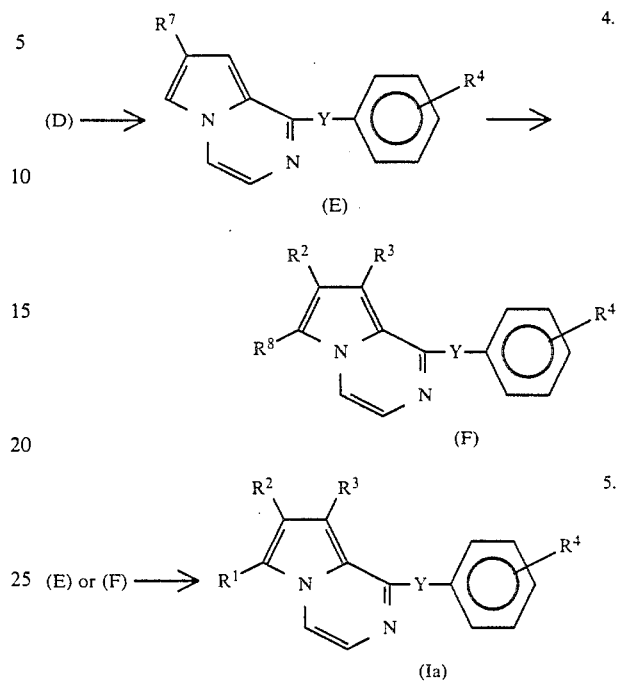

Compounds of formula (A) are prepared according to the methods described in *J. Org. Chem.* 1977, Vol. 42, No. 26, p. 4248.

2-Iodo-1,1-diethoxyethane used in Step 3 may be prepared according to methods known to one of ordinary skill in the art, e.g., by treating 2-bromo-1,1-diethoxyethane, which is commercially available, for example, from Aldrich Chemical Co., in a polar aprotic solvent, preferably acetone, with a solution of sodium iodide and sodium bicarbonate.

The compounds of formula (Ia) are prepared by first treating pyrrole with a compound of formula (A) (Step 1) in a non-polar solvent, for example dichloroethane, at temperatures of between 0° C. and 30° C., preferably at about 25° C., for about 8 to 20 hours, preferably for about 16 hours. The reaction mixture is then neutralized by the addition of an appropriate base, preferably sodium hydroxide to form a compound of formula (B). Compounds of formula (B) are then isolated from the reaction mixture by standard isolation techniques, preferably by column chromatography.

Compounds of formula (B) may then be brominated under conditions that give compounds of formula (C) where X is bromo (bromine in a non-polar aprotic solvent, preferably methylene chloride, at temperatures between about −80° C. and −70° C., preferably at about −78° C., for about 30 minutes to an hour, preferably for about 30 minutes). Alternatively, compounds of formula (B) may be chlorinated with an excess of sulfuryl chloride under conditions that give compounds of formula (C) where X is chloro (at initial temperatures of about −80° C. to −70°, preferably −78° C., then allowed to rise to room temperature while stirring for about 30 minutes to an hour). Compounds of formula (C) are then isolated using standard isolation techniques, preferably by column chromatography (Step 2).

Compounds of formulae (B) and (C) are then N-alkylated by treatment first with a 0° C. solution of sodium hydride in an anhydrous aprotic solvent, preferably dimethylformamide and then, after the temperature of the reaction mixture rises to room temperature and hydrogen is fully evolved, by addition of 2-iodo-1,1-diethoxyethane in an aprotic solvent, preferably dimethylformamide. The reaction mixture is allowed to reflux for 4 to 6 hours, preferably for 5 hours, to give compounds of formula (D) which are isolated from the reaction mixture by standard isolation techniques, preferably by column chromatography (Step 3).

Compounds of formula (D), dissolved in a protic solvent, preferably acetic acid, are then cyclized by treatment with an excess amount of ammonium acetate at reflux temperatures for about 2 to 4 hours to afford compounds of formula (E). Compounds of formula (E) are then treated with bromine in a protic solvent, preferably ethanol, under anhydrous conditions to form compounds of formula (F) wherein $R^8$ is bromo (Step 4). (Compounds of formula (F) wherein $R^3$ is halo are prepared by methods described in the following sections. Compounds of formula (F) wherein $R^2$ or $R^3$ is lower alkyl or lower alkylthio are prepared from the corresponding halo compounds by treatment with a lower alkyl halide or lower alkyldisulfides similar to the methods described in the following section.)

Compounds of formulae (E) or (F) wherein $R^8$ is hydrogen are then dissolved in an an polar aprotic solvent, preferably tetrahydrofuran, and treated with a lower alkylnitrite, preferably n-butylnitrite. The reaction mixture is then heated to reflux for 30 minutes to 1 hour, preferably 30 minutes. The resulting nitroso compounds are then dissolved in a protic solvent, preferably ethanol, and are then treated with a reducing agent, preferably stannous chloride, at room temperature to afford compounds of formula (Ia) wherein $R^1$ is —NH$_2$, which are isolated from the reaction mixture by conventional methods, preferably by extraction and column chromatography.

Compounds of formula (Ia) wherein $R^1$ is —NHR$^5$ are prepared by treating compounds of formula (Ia) wherein $R^1$ is —NH$_2$ with a small amount of paraformadehyde. A reducing agent, preferably sodium cyanoborohydride, is then added to the reaction mixture, which is then stirred for 30 minutes to an hour, preferably 30 minutes, at room temperature. The compounds of formula (Ia) wherein $R^1$ is —NHR$^5$ are then isolated from the reaction mixture by conventional methods, preferably by extraction and purification by column chromatography.

Compounds of formula (Ia) wherein $R^1$ is thiocyano are prepared by first adding a solution of bromine in methanol to a cooled solution (−78° C.) of potassium thiocyanate in a protic solvent, preferably methanol. The resulting reaction mixture is stirred at −78° C. for about 30 minutes to 1 hour, preferably for about 45 minutes. A solution of a compound of formulae (E) or (F) in a protic solvent, preferably methanol, is then added to the reaction mixture. The resulting reaction mixture is stirred at 0° C. for about 30 minutes to 1 hour, preferably for about 30 minutes. The reaction mixture is then poured into ice water and neutralized with a saturated solution of base, preferably sodium bicarbonate. Compounds of formula (Ia) wherein $R^1$ is thiocyano are then isolated from the reaction mixture by conventional methods, preferably by extraction with ethyl acetate and purification by column chromatography. Other compounds of formulae (F) and (Ia) wherein $R^3$ is thiocyano may be similarly prepared.

Alternatively, compounds of formula (Ia) are synthesized as shown in the following Reaction Scheme 1a wherein $R^8$ is hydrogen or bromo; and X is bromo or chloro:

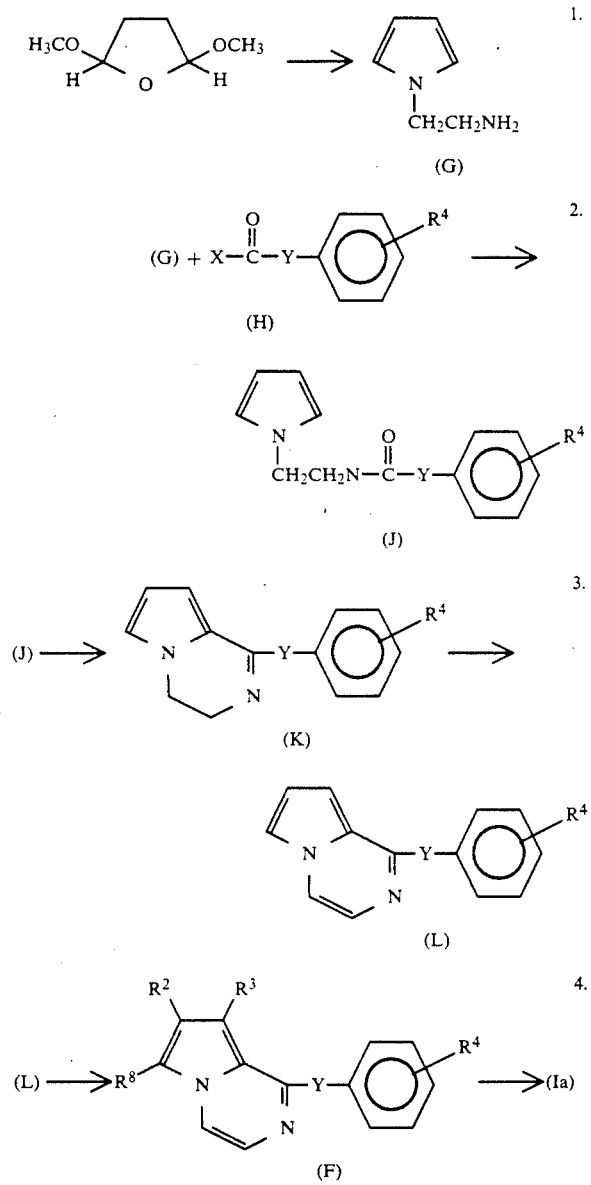

The ω-phenylalkanoyl halides of formula (H) are commercially available or may be prepared by methods known to those of ordinary skill in the art.

2,5-dimethoxytetrahydrofuran used in Step 1 is commercially available, for example, from Aldrich Chemical Co.

In general, compounds of formula (Ia) are alternatively prepared by first treating 2,5-dimethoxytetrahydrofuran with ethylene diamine in acetic acid/dioxane, followed by hydrolysis, according to the methods described in *Synthesis* 1981, pp. 481–483, to afford 1-(2-aminoethyl)pyrrole of formula (G) (Step 1).

1-(2-minoethyl)pyrrole is then treated with an ω-phenylalkanoyl halide of formula (H) in a neutral solvent, preferably benzene, at room temperature for about 30 minutes to 1 hour, preferably for 30 minutes to form compounds of formula (J), which are isolated from the reaction mixture by standard isolation techniques, preferably by extraction and concentration and then recrystallization (Step 2).

Compounds of formula (J) are then cyclized by treatment with phosphorous oxychloride according to the methods described in *Synthesis*, supra, to afford compounds of formula (K), which are isolated from the reaction mixture by column chromatography. Compounds of formula (K) are then dehydrogenated in an aromatic hydrocarbon solvent, preferably xylene, by a dehydrogenating agent, preferably 10% palladium over carbon, at reflux temperatures, to afford compounds of formula (L) (Step 3).

Compounds of formula (L) are then halogenated by conventional methods to form compounds of formula (F) wherein $R^8$, $R^2$ or $R^3$ are halo. Compounds of formula (F) wherein $R^8$ and $R^3$ are bromo or wherein $R^8$ is bromo and $R^3$ is chloro may be metallated as described below for compounds of formula (P) followed by quenching with water at $-72°$ C. to afford compounds of formula (F) wherein $R^8$ is hydrogen. Compounds of formula (F) wherein $R^2$ or $R^3$ are lower alkyl are prepared by metal-halogen exchanged as described below for compounds of formula (P) followed by treatment with lower alkyl halides or lower alkyl disulfides to afford compounds of formula (F) wherein $R^2$ or $R^3$ is lower alkyl or lower alkylthio.

Compounds of formula (F) wherein $R^8$ is hydrogen are then treated in the manner described above to afford compounds of formula (Ia) wherein $R^1$ is thiocyano, $-NH_2$ or $-NHR^5$.

B. Preparation of Compounds of Formula (Ib)

Compounds of formula (Ib) are compounds of formula (I) wherein $R^1$ is thiocyano, $-NH_2$ or $-NHR^5$; $R^2$, $R^3$ and $R^4$ are as defined above in the Summary of Invention; and Y is $-(CH_2)_n-$ where n is 2, 3 or 4. They are synthesized as shown in the following Reaction Scheme 2 wherein $R^8$ is hydrogen or bromo, X is bromo or chloro and Z is $-(CH_2)_n-$ where n is 1, 2 or 3:

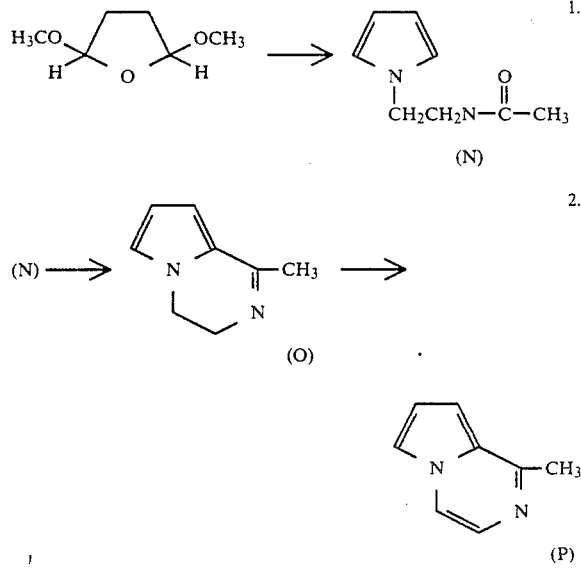

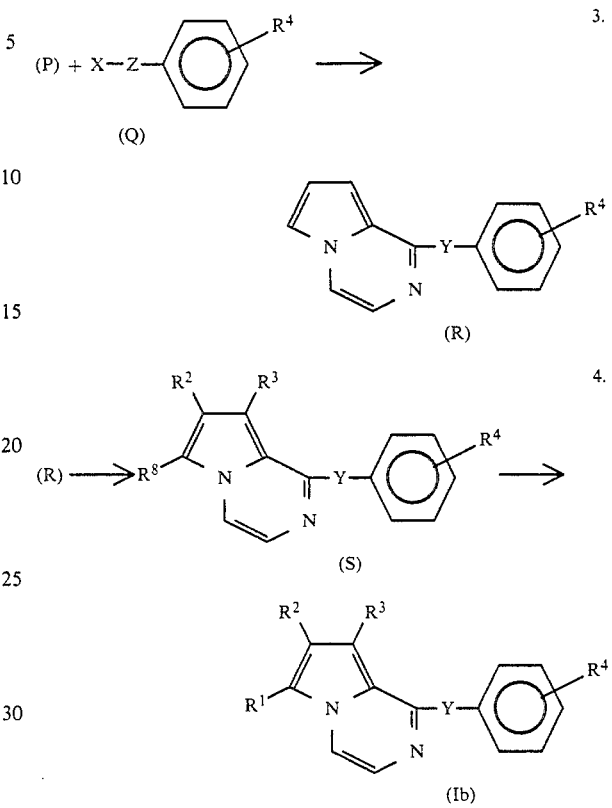

The ω-phenylalkyl halides of formula (Q) are commercially available, for example, from Aldrich Chemical Co., or may be prepared according to methods known to those of ordinary skill in the art.

In general, the compounds of formula (Ib) are prepared by first treating 2,5-dimethoxytetrahydrofuran with ethylenediamine under the conditions described in *Synthesis*, supra, to afford 1-(2-acetylaminoethyl)-pyrrole of formula (N) (Step 1).

1-(2-acetylaminoethyl)-pyrrole is then cyclized by treatment with phosphorous oxychloride according to the methods described in *Synthesis*, supra, to afford the compound of formula (O). This compound is then dehydrogenated with a dehydrogenating agent, preferably 10% palladium over carbon, to afford the compound of formula (P), which is isolated from the reaction mixture by conventional methods (Step 2).

The compound of formula (P) is then metallated by first treating the compound with an equimolar amount of a lower alkyl-alkaline metal reagent, preferably n-butyllithium, at temperatures between $-80°$ C. and $-75°$ C., preferably at about $-78°$ C., in an aprotic solvent, preferably tetrahydrofuran, for about 1 to 10 minutes, preferably for about 5 minutes. The reaction mixture is then warmed to room temperature and stirred for about 1 hour to 2 hours, preferably for about 1 hour. The reaction mixture is then cooled for the addition of the ω-phenylalkyl halides of formula (Q). The reaction mixture is then allowed to warm to room temperature and stirred for about 4 hours to 6 hours, preferably for about 6 hours to afford compounds of formula (R), which are then isolated from the reaction mixture by standard isolation techniques, preferably by extraction and column chromatography (Step 3).

Compounds of formula (R) are then treated in a similar manner as compounds of formulae (E) and (L) above to form compounds of formula (S).

Alternatively, compounds of formula (S) wherein $R^2$ is halo, preferably bromo or chloro, are prepared by halogenating 2-acetylpyrrole in a similar manner as compounds of formula (B) in Reaction Scheme 1 above to afford 4-halo-2-acetylpyrroles. These compounds are then treated with 2-iodo-1,1-diethoxyethane in a similar manner as compounds of formula (C) in Reaction Scheme 1 above. The resulting compounds are then cyclized in a similar manner as compounds of formula (D) in Reaction Scheme 1 above to afford 1-methyl-7-halopyrrolo[1,2-a]pyrazines. These compounds are then treated with an ω-phenylalkyl halide of formula (Q) in Reaction Scheme 2 above to afford compounds of formula (R) which are halogenated at the 7-position. These compounds are then used to prepare compounds of formula (S) as described above.

Compounds of formula (S) are then treated in a similar manner as the compounds of formula (F) above to form compounds of formula (Ib) wherein $R^1$ is thiocyano, $-NH_2$ or $-NHR^5$.

Compounds of formula (Ia) wherein Y is $-(CH_2)_n-$ where n is 2 may also be prepared by the foregoing synthesis.

C. Preparation of Compounds of Formula (Ic)

Compounds of formula (Ic) are compounds of formula (I) wherein $R^1$ is thiocyano, $-NH_2$ or $-NHR^5$; $R^2$, $R^3$ and $R^4$ are as defined above in the Summary of Invention and Y is $-OCH_2-$ or $-SCH_2-$. They are synthesized as shown in the following Reaction Scheme 3 wherein $R^8$ is hydrogen or bromo, and W is HO— or HS—:

REACTION SCHEME 3

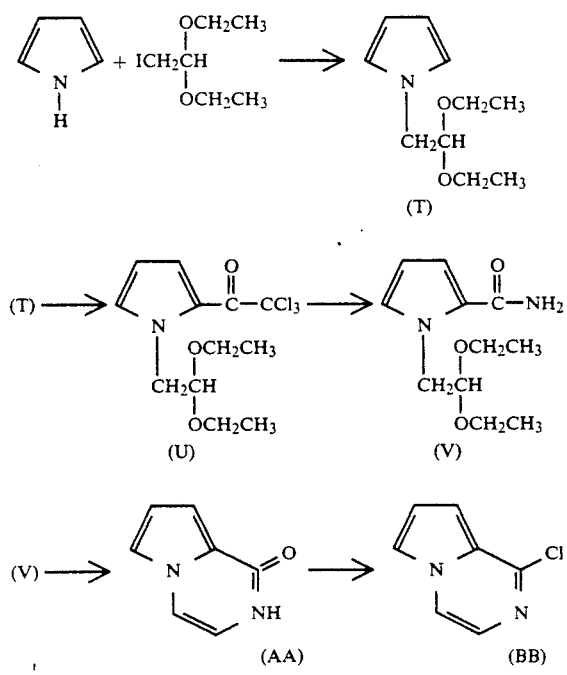

-continued
REACTION SCHEME 3

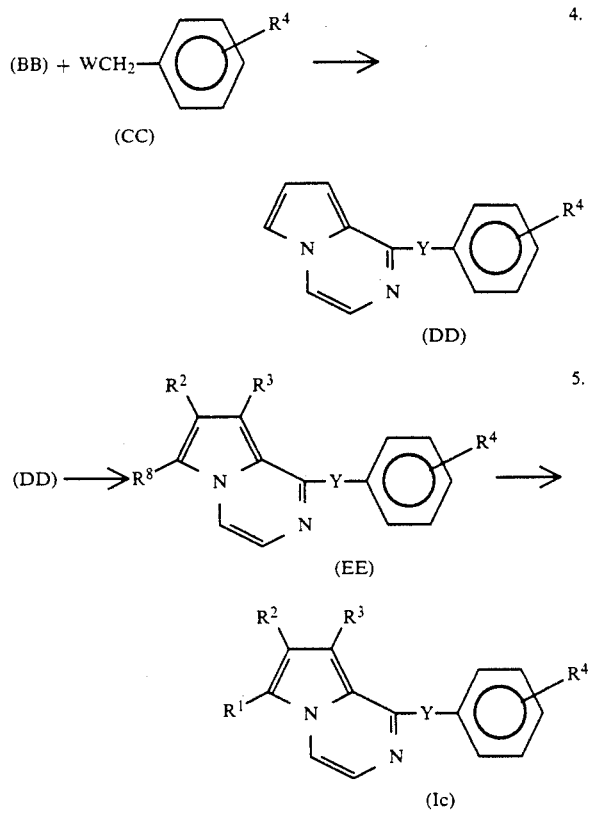

Benzyl alcohol and benzyl thiol of formula (CC) used in Step 4 are commercially available, for example, from Aldrich Chemical Co, or may be prepared according to methods known to one of ordinary skill in the art.

In general, compounds of formula (Ic) are prepared by first treating pyrrole with sodium hydride in an aprotic solvent, preferably dimethylformamide, at temperatures between −5° and 0° C. to form the anion. After hydrogen is fully evolved 2-iodo-1,1-dethoxyethane is added to the reaction mixture, which is then allowed to reflux for about 4 to 6 hours, preferably for about 5 hours, to afford the compound of formula (T), which is isolated from the reaction mixture by standard isolation techniques, preferably by extraction, and column chromatography (Step 1).

The compound of formula (T) is then acylated by treatment with trichloroacetyl chloride in the presence of 2,6-lutidine in an aprotic solvent, preferably chloroform, at reflux temperatures for about 16 to 20 hours, preferably for about 20 hours, to afford the compound of formula (U), which is isolated from the reaction mixture by standard isolation techniques, preferably by extraction and column chromatography. The compound of formula (U) is then amidated by treatment with sodamide in ammonia at temperatures of about −10° C. to form the compound of formula (V), which is isolated from the reaction mixture by standard isolation techniques, preferably by column chromatography (Step 2).

The compound of formula (V) is then cyclized by reflux in glacial acetic acid to form the compound of formula (AA). The compound of formula (AA) is then chlorinated at the 1-position by treatment with phosphorous oxychloride for about 12 hours to 16 hours, preferably for about 16 hours, to afford the compound of formula (BB) (Step 3).

The compound of formula (BB) is then treated with either a benzyl alcohol or benzyl thiol of formula (CC) in the presence of sodium hydride in an aprotic solvent, preferably dimethylformamide, at temperatures of about 95° C. to 105° C., preferably at about 100° C., for 30 minutes to an hour, preferably for 1 hour, to afford compounds of formula (DD), which are isolated from the reaction mixture by standard isolation techniques, preferably extraction and recrystallization (Step 4).

Compounds of formula (DD) are then treated in a similar manner as compounds of formulae (E), (L) and (R) to afford compounds of formula (EE) wherein $R^8$ is hydrogen or bromo, and $R^2$, $R^3$ and $R^4$ are as described above in the Summary of Invention.

Compounds of formula (EE) are then treated in a similar manner as compounds of formulae (F) and (S) above to form compounds of formula (Ic) wherein $R^1$ is thiocyano, $-NH_2$ or $-NHR^5$.

D. Preparation of Compounds of Formula (Id)

Compounds of formula (Id) are compounds of formula (I) wherein $R^1$ is thiocyano, $-NH_2$, or $NHR^5$, $R^2$, $R^3$ and $R^4$ are as defined above in the Summary of the the Invention, and Y is $-CH=CH-$. They are synthesized from compounds of formula (P) as shown in the following Reaction Scheme 4 wherein $R^8$ is hydrogen or bromo:

REACTION SCHEME 4

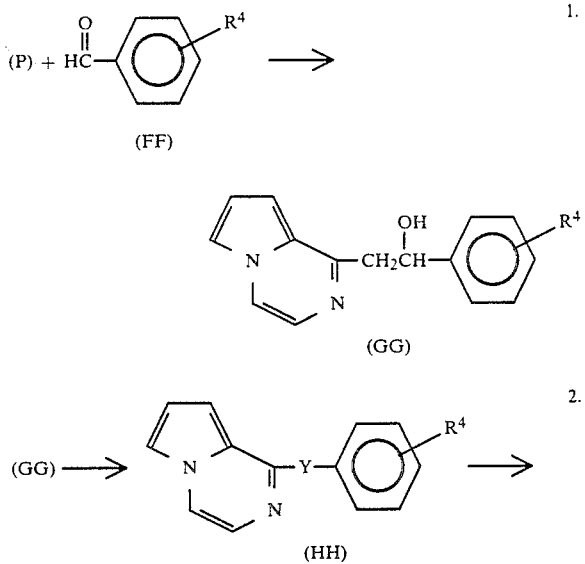

-continued
REACTION SCHEME 4

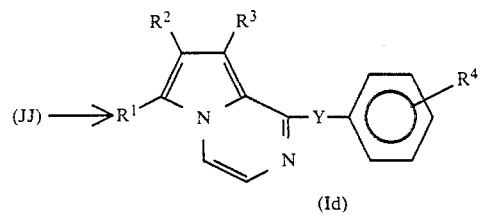

Compounds of formula (P) are prepared above in Reaction Scheme 2.

Substituted benzaldehydes of formula (FF) used in Step 1 are commercially available, for example, from Aldrich Chemical Co., or may be prepared by methods known to one of ordinary skill in the art.

In general, compounds of formula (Id) are prepared by first treating a solution of a compound of formula (P) in an anhydrous polar aprotic solvent, preferably tetrahydrofuran, with a substituted benzaldehyde of formula (FF) in a similar manner as in Reaction Scheme 2, Step 3, above, to afford compounds of formula (GG) (Step 1).

Compounds of formula (GG) are then treated with a solution of an equivalent amount of aqueous sulfuric acid in a non-polar aprotic solvent, preferably toluene. The reaction mixture is allowed to reflux for about 24 to about 48 hours, preferably for about 48 hours. After the reaction mixture is neutralized by the addition of an appropriate base, preferably ammonium hydroxide, compounds of formula (HH) are then isolated from the reaction mixture by conventional methods, preferably by extraction and purification by column chromatography. Compounds of formula (HH) are then treated in a similar manner as compound of formulae (E), (L) and (R) to form compounds of formula (JJ) (Step 2).

Compounds of formula (JJ) are then treated in a similar manner as the compounds of formulae (E), (F), (EE) and (S) above to form compounds of formula (Id) wherein $R^1$ is thiocyano, $-NH_2$ or $NHR^5$ and Y is $-CH=CH-$.

E. Preparation of Compounds of Formulae (Ie) and (If)

Compounds of formula (Ie) are compounds of formula (I) wherein $R^1$ is $-CH_2CN$ and $R^2$, $R^3$, $R^4$, $R^5$ and Y are as defined above in the Summary of Invention. Compounds of formula (If) are compounds of formula (I) wherein $R^1$ is $-CH_2OR^5$ and $R^2$, $R^3$, $R^4$, $R^5$ and Y are as defined above in the Summary of Invention. Compounds of formulae (Ie) and (If) are synthesized as shown in the following Reaction Scheme 4 wherein compounds of formula (KK) are compounds of formulae (F), (S), (EE) and (JJ) wherein $R^8$ is hydrogen:

REACTION SCHEME 5

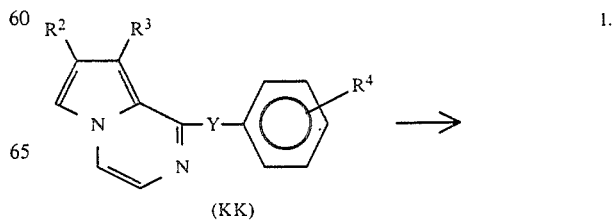

-continued
REACTION SCHEME 5

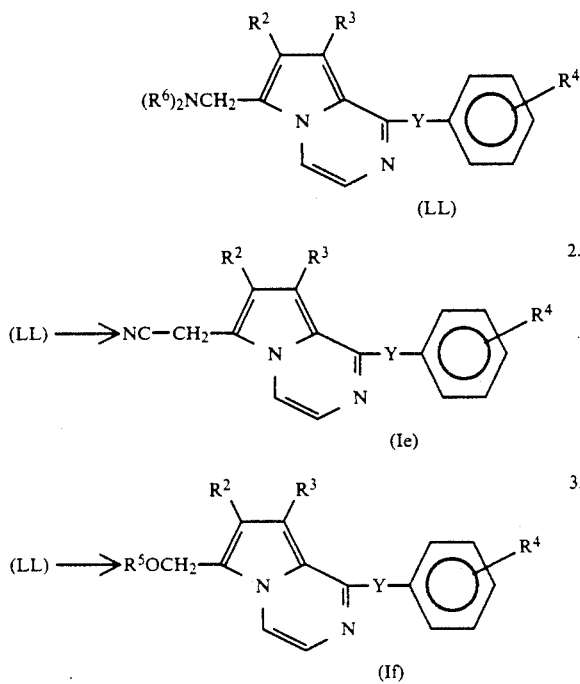

In general, compounds of formula (Ie) are prepared by a novel modification of the Mannich reaction. Paraformaldehyde is cracked by distilling it under atmospheric pressure and collecting the distillate in a flask containing dimethylamine hydrochloride at temperatures between $-80°$ C. and $-70°$ C., preferably at about $-78°$ C. The reaction mixture is then allowed to warm to room temperature for a few minutes and then cooled again to below $-40°$ C. Compounds of formula (KK), which are compounds of formulae (F), (S), (EE) or (JJ) wherein $R^8$ is hydrogen, are dissolved in an aprotic solvent, preferably anhydrous acetonitrile, and then added to the reaction mixture. The reaction mixture is stirred at room temperature for about 6 to 8 hours, preferably for about 8 hours. Extraction of the reaction mixture and purification of the product affords compounds of formula (LL) (Step 1).

Compounds of formula (LL) are then dissolved in a protic solvent, preferably methanol, and then treated with a lower alkyl halide, preferably by methyl iodide, at temperatures of about 0° C. to 5° C., preferably at 0° C. The reaction mixture is then stirred at room temperature for 4 to 6 hours, preferably for about 5 hours, to afford the appropriate quarternary salts, which are isolated from the reaction mixture by conventional methods. The quarternary salts are then dissolved in an aprotic solvent, preferably acetonitrile, and then treated with sodium cyanide in refluxing dimethylformamide for 2 to 4 hours, preferably for about 3 hours. After cooling, compounds of formula (Ie) are isolated from the reaction mixture by conventional methods, preferably extraction followed by column chromatography.

Compounds of formula (Ie) wherein $R^3$ is thiocyano are prepared by similar methods as described above for preparing compounds of formula (Ia) wherein $R^1$ is thiocyano.

Compounds of formula (Ie) wherein $R^3$ is alkylthio are prepared by treating compounds of formula (Ie) wherein $R^3$ is thiocyano in a mixture of a protic solvent, preferably methanol, and a non-polar aprotic solvent, preferably dichloromethane, with pulverized alkaline base, preferably potassium hydroxide. The reaction mixture is allowed to stir at room temperatures for a short period of time, preferably about 15 minutes, after which a lower alkylhalide or lower alkylmethanesulfonate is added. The resulting reaction mixture is allowed to stir at room temperature for about 2 to 4 hours, preferably for about 3 hours. Compounds of formula (Ie) wherein $R^3$ is alkylthio are then isolated from the reaction mixture by conventional methods, preferably by evaporation of solvents and purification by column chromatography.

Compounds of formula (Ie) wherein $R^3$ is halo are prepared by treating compounds of formula (Ie) wherein $R^3$ is hydrogen with certain halogenating agents under conditions that give rise to compounds wherein $R^3$ is halo. For example, compounds of formula (Ie) wherein $R^3$ is hydrogen are treated with either a brominating agent, preferably N-bromosuccinimide to form compounds of formula (Ie) wherein $R^3$ is bromo, or with a chlorinating agent, preferably sulfuryl chloride, to form compounds of formula (Ie) wherein $R^3$ is chloro. Such compounds are isolated from the respective reaction mixtures by conventional methods, preferably by extraction followed by purification by column chromatography.

Compounds of formula (Ie) wherein $R^4$ is lower alkylsulfonyl are prepared by treating compounds of formula (Ie) wherein $R^2$ and $R^3$ are other than alkylthio and $R^4$ is alkylthio (as prepared by methods described above) in an non-polar, aprotic solvent, preferably dichloroethane, with an oxidizing agent, preferably m-chloroperbenzoic acid, at room temperatures for about 2 to 4 hours, preferably for about 3 hours. The compounds of formula (Ie) wherein $R^4$ is lower alkylsulfonyl are then isolated from the reaction mixture by conventional methods, preferably by extraction and purification by column chromatography.

Alternatively, the quarternary salts of compounds of formula (LL) are treated with an excess of an alkaline metal alkoxide, preferably sodium ethoxide. The reaction mixture is then refluxed for 10 to 20 minutes, preferably 15 minutes. After cooling, compounds of formula (If) are isolated from the reaction mixture by conventional methods, preferably by extraction with ethyl acetate and purification by column chromatography (Step 3).

In summary, the compounds of formula (I) are prepared by:

(1) treating a compound of formulae (E), (F), (S), (EE) or (JJ) wherein $R^8$ is hydrogen with a nitrating agent to form a compound of formulae (Ia), (Ib), (Ic) or (Id) wherein $R^1$ is $-NH_2$ or $-NHR^5$; or (2) treating a compound of formulae (E), (F), (S), (EE) or (JJ) wherein $R^8$ is hydrogen with a thiocyanating agent to form a compound of formulae (Ia), (Ib), (Ic) or (Id) wherein $R^1$ is thiocyano; or (3) treating a quarternary salt of a compound of formula (LL) with sodium cyanide to form a compound of formula (Ie) wherein $R^1$ is $-CH_2CN$; or (4) treating a quarternary salt of a compound of formula (LL) with an alkaline metal alkoxide to form a compound of formula (If) wherein $R^1$ is $-CH_2OR^5$.

The following specific examples are provided as a guide to assist in the practice of the invention, and are not intended as a limitation on the scope of the invention.

PREPARATION 1

2-(3-phenylpropanoyl)pyrrole (A compound of formula (B))

A. To 3-phenylpropanoyl morpholide (30 g, 137 mmol), a compound of formula (A), phosphorous oxychloride (55 g, 359 mmol, 2.6 eq.) was added dropwise and the solution was stirred for 8 hours at room temperature. The resulting mixture was cooled to 0° C. and a solution of pyrrole (10 g, 150 mmol) in 500 mL of 1,2-dichloroethane was slowly added. The resulting mixture was stirred for 16 hours at room temperature, then transferred to a beaker and neutralized with a 25% solution of sodium hydroxide (400 mL) which was added slowly with vigorous stirring. The organic phase was then separated and the aqueous phase was extracted with 1,2-dichloroethane (2×100 mL). The combined organic extracts were dried over MgSO4 and concentrated. Purification was carried out by column chromatography [silica gel, 200 g, hexane:ethyl acetate (1:1)] to give 15.8 g (58%) of the title compound, 2-(3-phenylpropanoyl)pyrrole, as a solid, m.p. 64°-66° C.

B. In a similar manner, but replacing 3-phenylpropanoyl morpholide with other appropriately substituted morpholides, the following compounds were made:
2-(3-chlorobenzoyl)pyrrole;
2-(4-methylbenzoyl)pyrrole, m.p. 114°-116° C; and
2-(4-chlorobenzoyl)pyrrole.

C. In a similar manner, but replacing 3-phenylpropanoyl morpholide with other appropriately substituted morpholides, the following compounds are made:
2-(3-bromobenzoyl)pyrrole;
2-(4-methoxybenzoyl)pyrrole;
2-(2-chlorobenzoyl)pyrrole;
2-(4-methylthiobenzoyl)pyrrole;
2-(3-iodobenzoyl)pyrrole;
2-(3-propoxybenzoyl)pyrrole;
2-(4-n-butylthiobenzoyl)pyrrole; and
2-(3-n-propylbenzoyl)pyrrole.

PREPARATION 2

2-(3-phenylpropanoyl)-4-bromopyrrole (A compound of formula (C))

A. A solution of 2-(3-phenylpropanoyl)pyrrole (2 g, 10 mmol) in dichloromethane (100 mL) was cooled to −78° C. and a solution of bromine (2 g, 12.5 mmol, 1.25 eq.) in dichloromethane (25 mL) was slowly added (30 minutes). After the addition, the reaction was stirred for 15 more minutes and poured onto $H_2O$ (100 mL). The two layers were separated and the aqueous layer was extracted with dichloromethane (2×25 mL). The combined extracts were dried over MgSO4, concentrated, and purified by column chromatography [silica gel, 70 g, hexane:ethyl acetate, (90:10)] to give 2.3 g (82%) of the title compound, 2-(3-phenylpropanoyl)-4-bromopyrrole, as a solid, m.p. 107°-107° C.

PREPARATION 3

2-(3-phenylpropanoyl)-4-chloropyrrole (A compound of formula (C))

A. A solution of 2-(3-phenylpropanoyl)pyrrole (3 g, 15.1 mmol) in dry $CH_2Cl_2$ (30 mL) was cooled to −78° C., and sulfuryl chloride (2.41 g, 1.45 mL, 18.1 mmol) was added dropwise. The temperature was allowed to rise to 0° C. and the reaction stirred for 30 minutes. The mixture was poured into ice (50 g) and a 1M solution of NaOH (30 mL) and then extracted with $CH_2Cl_2$ (2×50 mL). The organic extracts were then washed with a saturated solution of NaCl (25 mL), dried over MgSO4 and concentrated. The residue was purified by column chromatography [silica gel, 60 g, hexane-ethyl acetate (8:2)] to give 1.38 g (39%) of the title compound, 2-(3-phenylpropanoyl)-4-chloropyrrole, m.p. 81°-82° C.

B. In a similar manner, but replacing 2-(3-phenylpropanoyl)pyrrole with 2-acetylpyrrole, the following compound was made:
2-acetyl-4-chloropyrrole, m.p. 124°-125° C.

PREPARATION 4

1-(2,2-diethoxyethyl)-2-(3-phenylpropanoyl)-4-bromopyrrole (A compound of formula (D))

A. To a suspension of 50% NaH in mineral oil (85 mg, 1.77 mmol) in 5 mL of dry DMF (0° C.), 2-(3-phenylpropanoyl)-4-bromopyrrole (450 mg, 1.61 mmol) in 20 mL of dry DMF was added dropwise. The reaction mixture was allowed to come to room temperature and when hydrogen evolution was complete, 2-iodo-1,1-diethoxyethane (0.393 g, 1.61 mmol) in 5 mL of dry dimethylformamide was added. The reaction mixture was heated to reflux for 5 hours or until there was no further advance of the reaction. The reaction mixture was cooled to room temperature, poured onto 50 mL of water, extracted with ether (2×50 mL), dried over MgSO4, and concentrated. The residue was purified by column chromatography [silica gel, 25 g, ethyl acetate:hexane (2:8)] to give 390 mg (77%) of the title compound, 1-(2,2-diethoxyethyl)-2-(3-phenylpropanoyl)-4-bromopyrrole, as an oil, ms 393, 395 (M+).

B. In a similar manner, but replacing 2-(3-phenylpropanoyl)-4-bromopyrrole with the appropriately substituted pyrrole:
1-(2,2-diethoxyethyl)-2-(3-phenylpropanoyl)-4-chloropyrrole, as an oil, NMR: (CHCl3) 1.17(t, 6H, J=6.1 Hz); 3.03(s, 4H); 3.31-3.85(m, 4H); 4.31(d, 2H, J=4.6 Hz); 4.51(t, 1H, J=4.6 Hz); 6.86(s, 2H, H-3, H-5 pyrrole); 7.10-7.38(m, 5H, phenyl);
1-(2,2-diethoxyethyl)-2-(4-chlorobenzoyl)pyrrole, as an oil, ms 321 (M+);
1-(2,2-diethoxyethyl)-2-(4 methylbenzoyl)pyrrole, as an oil, ms 301 (M+);
1-(2,2-diethoxyethyl)-2-acetyl-4-chloropyrrole, ms 259 (M+); and
1-(2,2-diethoxyethyl)-2-(3-chlorobenzoyl)pyrrole, as an oil, ms 321 (M+).

C. In a similar manner, but replacing 2-(3-phenylpropanoyl)-4-bromopyrrole with the appropriately substituted pyrrole, the following compounds are made:
1-(2,2-diethoxyethyl)-2-(3-phenylpropanoyl)pyrrole;
1-(2,2-diethoxyethyl)-2-(3-(4-methoxyphenyl)-propanoyl)pyrrole;
1-(2,2-diethoxyethyl)-2-(3-(4-methylthiophenyl)-propanoyl)pyrrole;
1-(2,2-diethoxyethyl)-2-(3-(4-n-butylphenyl)-propanoyl)pyrrole; and
1-(2,2-diethoxyethyl)-2-(3-(3-chlorophenyl)propanoyl)-pyrrole.

PREPARATION 5

1-(2-phenylethyl)-7-bromopyrrolo[1,2-a]pyrazine (A compound of formula (E))

A. 1-(2,2-diethoxyethyl)-2-(3-phenylpropanoyl)-4-bromopyrrole (250 mg, 0.64 mmol) was dissolved in previously distilled acetic acid (20 mL). Ammonium acetate (1 g, 12.9 mmol, 20 eq.) was then added to the reaction mixture, and the mixture was heated to reflux for 2 hours. The reaction mixture was then poured into ice-water (10 g) and neutralized with a 25% solution of NaOH to a pH of 10. The reaction mixture was extracted with ethyl acetate (2×30 mL). The organic extracts were combined, dried over MgSO$_4$, concentrated and purified by column chromatography (silica gel, 25 g, ethyl acetate) to give 164 mg (85%) of the title compound, 1-(2-phenylethyl)-7-bromopyrrolo[1,2-a]pyrazine, as an oil, ms 300, 302 (M+).

B. In a similar manner, but replacing 1-(2,2-diethoxyethyl)-2-(3-phenylpropanoyl)-4-bromopyrrole with other 1-(2,2-diethoxyethyl)pyrroles, the following compounds were made:

1-(2-phenylethyl)-7-chloropyrrolo[1,2-a]pyrazine, ms 256 (M+);

1-(4-chlorophenyl)pyrrolo[1,2-a]pyrazine, m.p. 105°–106° C.;

1-(4-methylphenyl)pyrrolo[1,2-a]pyrazine, m.p. 77°–77° C.;

1-methyl-7-chloropyrrolo[1,2-a]pyrazine, m.p. 55°–56° C.; and 1-(3-chlorophenyl)pyrrolo[1,2-a]pyrazine, m.p. 92°–93° C.

C. In a similar manner, but replacing 1-(2,2-diethoxyethyl)-2-(3-phenylpropanoyl)-4-bromopyrrole with other appropriately substituted pyrroles the following compounds are made:

1-(2-(4-bromophenyl)ethyl)pyrrolo[1,2-a]pyrazine;
1-(2-(3-methoxyphenyl)ethyl)pyrrolo[1,2-a]pyrazine;
1-(2-(4-n-butylphenyl)ethyl)pyrrolo[1,2-a]pyrazine;
1-(2-(3-ethoxyphenyl)ethyl)pyrrolo[1,2-a]pyrazine;
1-(2-(2-chlorophenyl)ethyl)pyrrolo[1,2-a]pyrazine;
1-(2-(4-ethylthiophenyl)ethyl)pyrrolo[1,2-a]pyrazine;
1-(4-ethylphenyl)pyrrolo[1,2-a]pyrazine; and
1-(4-methoxyphenyl)pyrrolo[1,2-a]pyrazine.

PREPARATION 6

1-(2-aminoethyl)pyrrole (The compound of formula (G))

A mixture of 2,5-dimethoxytetrahydrofuran (90 g, 680 mmol), ethylenediamine (36 g, 600 mmol), acetic acid (600 ml), and dioxane (800 mL) was heated under reflux for 4 hours, and then stirred at room temperature overnight. The volatiles were removed under reduced pressure and the residue was made basic with a 50% solution of potassium hydroxide (400 mL) and refluxed for 5 hours. The cooled aqueous solution was then extracted with chloroform (3×300 mL). The combined extracts were evaporated and separated via an acid/base extraction (1M, HCl solution, 400 mL) to give 38.3 g of the title compound, 1-(2-aminoethyl)pyrrole (58%), as a dark brown oil.

PREPARATION 7

1-(2-(N-(3-phenylpropanoyl)amino)ethyl)pyrrole (A compound of formula (J))

A. To a solution of 1-(2-aminoethyl)pyrrole (36 g, 327 mmol) and triethylamine (49.6 g, 490 mmol) in 300 mL of dry benzene was added dropwise 3-phenylpropanoyl chloride (60.7 g, 359.7 mmol) in 100 mL of dry benzene. The reaction mixture was stirred for 30 minutes and then neutralized with a 1M solution of sodium hydroxide (300 ml). The organic phase was separated and the aqueous phase was extracted with benzene (2×100 mL). The combined extracts were dried over MgSO$_4$ and concentrated. The residue was recrystallized (ether:hexane) to give 69.7 g (88%) of the title compound, 1-(2-(N-3-phenylpropanoyl)amino)ethyl)pyrrole, m.p. 97°–99° C.

B. In a similar manner, but replacing 3-phenylpropanoyl chloride with other appropriately substituted ω-phenylalkanoyl halides, the following compounds were made:

1-(2-(N-(4-methoxybenzoyl)amino)ethyl)pyrrole, m.p. 109°–111° C.;

1-(2-(N-(4-methylthiobenzoyl)amino)ethyl)pyrrole, m.p. 116°–118° C.; and 1-(2-(N-benzoylamino)ethyl)pyrrole, m.p. 103°–105° C.

C. In a similar manner, but replacing 3-phenylpropanoyl chloride with other appropriately substituted ω-phenylalkanoyl halides, the following compounds are made:

1-(2-(N-(3-(4-methoxyphenyl)propanoyl)amino)ethyl)pyrrole;

1-(2-(N-(3-(3-chlorophenyl)propanoyl)amino)ethyl)pyrrole;

1-(2-(N-(3-(2-ethylphenyl)propanoyl)amino)ethyl)pyrrole;

1-(2-(N-(3-(4-methylthiophenyl)propanoyl)amino)ethyl)pyrrole;

1-(2-(N-(3-(4-n-butylthiophenyl)propanoyl)amino)ethyl)pyrrole; and 1-(2-(N-(4-phenylbutanoyl)amino)ethyl)pyrrole.

PREPARATION 8

1-(2-phenylethyl)-3,4-dihydropyrrolo[1,2-a]pyrazine (A compound of formula (K))

A. To 1-(2-(3-phenylpropanoylamino)ethyl)pyrrole (60 g, 248 mmol) was added, with stirring and in small portions, phosphorous oxychloride (114.1 g, 744 mmol, 69.4 mL) at 20° C. The resulting solution was heated under reflux for 3 hours and evaporated under reduced pressure. The residue was partitioned between 10% aqueous sodium hydroxide and ether until basic, pH=10. The organic phase was then separated and the aqueous phase was extracted with ether (2×300 mL). The combined organic extracts were dried over MgSO$_4$ and evaporated under reduced pressure. The residue was purified by column chromatography (neutral alumina, 300 g, CHCl$_3$) to give 45.8 g (82%) of the title compound, 1-(2-phenylethyl)-3,4-dihydropyrrolo[1,2-a]pyrazine.

B. In a similar manner, but replacing 1-(2-(3-phenylpropanoylamino)ethyl)pyrrole with the appropriately substituted pyrrole, the following compounds were made:

1-(4-methoxyphenyl)-3,4-dihydropyrrolo[1,2-a]pyrazine, m.p. 89°–90° C.;

1-(4-methylthiophenyl)-3,4-dihydropyrrolo[1,2-a]pyrazine, m.p. 82°-84° C.; and 1-phenyl-3,4-dihydropyrrolo[1,2-a]pyrazine, ms 196 (M+).

C. In a similar manner, but replacing 1-(2-(3-phenylpropanoylamino)ethyl)pyrrole with the appropriately substituted pyrrole, the following compounds are made:

1-(2-(4-methoxyphenyl)ethyl)-3,4-dihydropyrrolo[1,2-a]pyrazine;

1-(2-(4-chlorophenyl)ethyl)-3,4-dihydropyrrolo[1,2-a]pyrazine;

1-(2-(2-ethylphenyl)ethyl)-3,4-dihydropyrrolo[1,2-a]pyrazine;

1-(2-(3-methylthiophenyl)ethyl-3,4-dihydropyrrolo[1,2-a]pyrazine;

1-(2-(4-n-butylthiophenyl)ethyl-3,4-dihydropyrrolo[1,2-a]pyrazine; and 1-(3-phenylpropyl)-3,4-dihydropyrrolo[1,2-a]pyrazine.

PREPARATION 9

1-(2-phenylethyl)pyrrolo[1,2-a]pyrazine (A compound of formula (L))

A. A mixture of 1-(2-phenylethyl)-3,4-dihydropyrrolo-[1,2-a]pyrazine (3 g, 13.4 mmol) and 10% Pd/C (3 g) in 40 mL of xylene was heated to reflux for 24 hours. The mixture was allowed to cool, filtered through celite. The filtrate was evaporated under vacuum and the residue was purified by column chromatography [silica gel, 60 g, hexane:ethyl acetate (60:40)] to give 2.43 g (81%) of the title compound, 1-(2-phenylethyl)pyrrolo[1,2-a]pyrazine, m.p. 79°-80° C.

B. In a similar manner, but replacing 1-(2-phenylethyl)-3,4-dihydropyrrolo[1,2-a]pyrazine with other appropriately substituted 3,4-dihydropyrrolo[1,2-a]pyrazines, the following compounds were made:

1-(4-methoxyphenyl)pyrrolo[1,2-a]pyrazine, m.p. 91°-93° C.; and 1-(4-methylthiophenyl)pyrrolo[1,2-a]pyrazine, m.p. 71°-73° C.

1-phenylpyrrolo[1,2-a]pyrazine, m.p. 72°-74° C.

C. In a similar manner, but replacing 1-(2-phenylethyl)-3,4-dihydropyrrolo[1,2-a]pyrazine with other appropriately substituted 3,4-dihydropyrrolo[1,2-a]pyrazines, the following compounds are made:

1-(2-(2-ethylphenyl)ethyl)pyrrolo[1,2-a]pyrazine;

1-(2-(3-methylthiophenyl)ethylpyrrolo[1,2-a]pyrazine;

1-(2-(4-n-butylthiophenyl)ethylpyrrolo[1,2-a]pyrazine; and 1-(3-phenylpropyl)pyrrolo[1,2-a]pyrazine.

PREPARATION 10

1-(2-acetylaminoethyl)pyrrole (The compound of formula (N))

A solution of 2,5-dimethoxytetrahydrofuran (90 g, 680 mmol) ethylenediamine (36 g, 600 mmol), acetic acid (600 mL), and dioxane (800 mL) was heated under reflux for 4 hours, and then stirred at room temperature overnight (16 hours). The volatiles were then removed under reduced pressure. The residue was then dissolved in CHCl3 (500 mL), and then washed with a 10% aqueous solution of sodium bicarbonate (300 mL) and water (300 mL). The organic extract was then dried over MgSO4, and evaporated. The product was then purified by column chromatography [silica gel 600 g, ethyl acetate:hexane (1:1)] to give 62 g (68%) of the title compound, 1-(2-acetylaminoethyl)pyrrole, m.p. 49°-51° C.

PREPARATION 11

1-methyl-3,4-dihydropyrrolo[1,2-a]-pyrazine (The compound of formula (O))

To 1-(2-acetylaminoethyl)pyrrole (16 g, 105 mmol), phosphorous oxychloride (55 g, 357 mmol, 90 mL) was added dropwise. The reaction was then heated to reflux for 3 hours. The phosphorous oxychloride was then removed at reduced pressure. The residue was then partitioned between 10% aqueous sodium hydroxide and ether (200 mL: 400 mL). The organic phase was dried over MgSO4, and evaporated. The resulting oil was filtered through a column of neutral alumina to give 12.1 g (88%) of the title compound, 1-methyl-3,4-dihydropyrrolo[1,2-a]pyrazine, as an oil, b.p. 105°-107° C./0.2 mm.

PREPARATION 12

1-methylpyrrolo[1,2-a]pyrazine (A compound of formula (P))

To a solution of 1-methyl-3,4-dihydropyrrolo[1,2-a]-pyrazine (12 g, 91 mmol) in xylene (100 mL) was added 12 g of 10% Pd/C. The mixture was refluxed for 8 hours. The mixture was then cooled and filtered through celite. The filtrate was evaporated at reduced pressure and the residue was recrystallized (ether-hexane) to give 11 g (93%) of the title compound, 1-methylpyrrolo[1,2-a]pyrazine, b.p. 102°-103° C./10 mm.

B. In a similar manner, but replacing 1-methyl-3,4-dihydropyrrolo[1,2-a]pyrazine with 1-phenyl-3,4-dihydropyrrolo[1,2-a]pyrazine, the following compound was made:

1-phenylpyrrolo[1,2-a]pyrazine, m.p. 72°-74° C.

PREPARATION 13

1-(2-phenylethyl)pyrrolo[1,2-a]pyrazine (A compound of formula (R))

A. A solution of 1-methylpyrrolo[1,2-a]pyrazine (10 g, 76 mmol) in 150 mL of dry THF was cooled to −78° C. and then treated with n-butyllithium (34.8 mL, 2.4M, 1.1 eq.). The reaction mixture was warmed to −10° C. and stirred at that temperature for one hour. The reaction mixture was cooled again to −78° C. and benzyl bromide (15.6 g, 91.2 mmol, 1.2 eq., 10.9 mL) in 50 mL of dry THF was added dropwise. The temperature of the reaction mixture was allowed to rise to room temperature and the reaction mixture was then stirred for one hour at room temperature. The reaction mixture was then poured onto a saturated solution of ammonium chloride (150 mL). The organic phase was separated and the aqueous phase extracted with ether (2×100 mL). The combined organic extracts were then washed with a saturated solution of NaCl (100 mL), dried over MgSO4, and evaporated. The residue was purified by column chromatography [silica gel, 100 g, hexane:ethyl acetate (8:20)] to give 14 g (83%) of the title compound, 1-(2-phenylethyl)pyrrolo[1,2-a]pyrazine, m.p. 80°-82° C.

B. In a similar manner, but replacing benzyl bromide with other appropriately substituted ω-phenylalkyl halides, the following compounds were made:

1-(3-phenylpropyl)pyrrolo[1,2-a]pyrazine, as a slightly yellow oil, ms 236 (M+);

1-(4-phenylbutyl)pyrrolo[1,2-a]pyrazine, m.p. 45°–46° C.;

1-(2-(4-methylphenyl)ethyl)pyrrolo[1,2-a]pyrazine, as an oil, NMR: (CDCl$_3$) 3.30(s, 3H); 3.00–3.41(m, 4H); 6.70–6.90(m, 2H, H-7, H-8 pyrrole); 7.03–7.42(m, 5H, H-6 pyrrole, phenyl); 7.68(d, 1H, H-3 pyrazine, J=4.8 Hz); 7.76(d, 1H, H-4 pyrazine, J=4.8 Hz);

1-(2-(4-chlorophenyl)ethyl)pyrrolo[1,2-a]pyrazine, m.p. 63°–64° C.;

1-(2-(4-methoxyphenyl)ethyl)pyrrolo[1,2-a]pyrazine, as a slightly yellow oil, ms 252 (M+);

1-(2-(2-methoxyphenyl)ethyl)pyrrolo[1,2-a]pyrazine, as a yellow oil, ms 252 (M+); and 1-(2-(4-methylthiophenyl)ethylpyrrolo[1,2-a]pyrazine, as an oil, ms 268 (M+).

C. In a similar manner, but replacing benzyl bromide with 4-chlorobenzylchloride, and replacing 1-methyl-pyrrolo[1,2-a]pyrazine with 1-methyl-7-chloropyrrolo[1,2-a]pyrazine, the following compound was made:

1-(2-(4-chlorophenyl)ethyl)-7-chloropyrrolo[1,2-a]pyrazine, m.p. 88°–89° C.

PREPARATION 14

1-(2-phenylethyl)-8-bromopyrrolo[1,2-a]pyrazine (Compounds of formulae (F), (M), (S) or (EE))

A. A solution of 1-(2-phenylethyl)-6,8-dibromopyrrolo[1,2-a]pyrazine (1 g, 2.6 mmol), in anhydrous THF (50 ml) was cooled to −78° C. and n-butyllithium (2.6 mmol, 1.6 mL of a solution 1.63M in cyclohexane) was added. The reaction was stirred for 10 minutes at −78° C., and 5 mL of water were added. The phases were separated, and the aqueous phase was extracted with ether (2×10 mL). The combined extracts were dried (MgSO$_4$), concentrated and purified by column chromatography [silica gel, 1 50 g, hexane-ethyl acetate (75:25)] to give 760 mg (96%) of the title compound, 1-(2-phenylethyl)-8-bromopyrrolo[1,2-a]pyrazine, as slightly yellow solid, m.p. 98°–99° C.

B. In a similar manner, but replacing 1-(2-phenylethyl)-6,8-dibromopyrrolo[1,2-a]pyrazine with the appropriately substituted 6-bromopyrrolo[1,2-a]pyrazine, the following compounds were made:

1-(2-phenylethyl)-8-chloropyrrolo[1,2-a]pyrazine, m.p. 104°–105° C.; and 1-(2-phenylethyl)-7-methyl-8-bromopyrrolo[1,2-a]pyrazine, m.p. 95°–96° C.

PREPARATION 15

2-iodo-1,1-diethoxyethane

To a solution of sodium bicarbonate (426.2 g, 5074 mmol) in acetone was added sodium iodide (760.3 g, 5074 mmol) and 2-bromo-1,1-diethoxyethane (500 g, 2537 mmol). The reaction mixture was allowed to reflux for 8 hours. The reaction mixture was then filtered and the solvent evaporated. Ether was added and the reaction mixture filtered again. The ether was evaporated, leaving the title compound, 2-iodo-1,1-diethoxyethane, as an oil, which was further purified by column chromatography.

PREPARATION 16

1-(2,2-diethoxyethyl)pyrrole (A compound of formula (T))

To a cold solution (−5° C. to 0° C.) of sodium hydride in anhydrous dimethylformamide (11.8 g, 245.9 mmol), pyrrole (15.0 g, 223.6 mmol) in dry dimethylformamide was slowly added while stirring vigorously. The reaction was completed, and the temperature raised to room temperature. After hydrogen is fully evolved, iodoacetaldehyde diethyl acetal was added (65.5 g, 268.1 mmol) to the reaction mixture. The reaction mixture was allowed to reflux for 5 hours or until there was no further advance of the reaction. The reaction mixture was cooled to room temperature, poured onto 50 mL of water, extracted with ether, dried over MgSO$_4$, and concentrated. The product was purified by column chromatography [silica gel, hexane] to give the title compound, 1-(2,2-diethoxyethyl)pyrrole, (95%), ms 183 (M+).

PREPARATION 17

1-(2,2-diethoxyethyl)-2-trichloroacetylpyrrole (A compound of formula (U))

To a refluxing solution of 1-(2,2-diethoxyethyl)pyrrole (31.6 g, 172.5 mmol) and 2,6-lutidine (20.3 g, 189.8 mmol) in 90 mL of chloroform over a period of 16 hours was added trichloroacetyl chloride (34.5 g, 189.8 mmol) in 90 mL of chloroform. The reaction mixture was refluxed for an additional 4 hours. The reaction mixture was allowed to cool to room temperature and then poured into a mixture of water and chloroform (1:1). The phases were separated, washed with a saturated solution of NaCl, dried over MgSO$_4$, and then evaporated. Purification of the product by column chromatography [hexane:ether (9.9:0.1)] gave the title compound, 1-(2,2-diethoxyethyl)-2-trichloroacetylpyrrole, in 60% yield, ms 327 (M+).

PREPARATION 18

1-(2,2-diethoxyethyl)pyrrole-2-carboxamide (A compound of formula (V))

To approximately 15 mL of anhydrous ammonia (dried by distillation over sodium) was added sodium (0.23 g, 10.0 mmol) in small pieces and a small amount of ferric chloride. The reaction was completed when the reaction mixture color changed from blue to gray. To the reaction mixture was then added 1-(2,2-diethoxyethyl)-2-trichloroacetylpyrrole (1.5 g, 4.56 mmol) in anhydrous THF. Water is then added slowly to the reaction mixture, which was then extracted with ether. Purification of the product by column chromatography [hexane:ether (1:1)] gave the title compound, 1-(2,2-diethoxyethyl)pyrrole-2-carboxamide, m.p. 75°–76° C.

PREPARATION 19 pyrrolo[1,2-a]pyrazin-1(2H)-one (A compound of formula (AA))

1-(2,2-diethoxyethyl)pyrrole-2-carboxamide (3.0 g, 13.2 mmol) was dissolved in glacial acetic acid. The reaction mixture was allowed to reflux and the reaction was continued by thin layer chromatography in a 100% ether system. At the end of the reaction, the reaction mixture was made basic with a 2N solution of sodium hydroxide. The reaction mixture was then extracted with ethyl acetate, washed with a saturated sodium bicarbonate solution, dried over MgSO$_4$ and evaporated. The product was purified by recrystallization in CH$_2$Cl$_2$-hexane to give the title compound, pyrrolo[1,2-a]pyrazin-1(2H)-one (80%), m.p. 227°–228° C.

PREPARATION 20

1-chloropyrrolo[1,2-a]pyrazine (A compound of formula (BB))

To pyrrolo[1,2-a]pyrazin-1(2H)-one (0.35 g, 2.61 mmol) was added phosphorous oxychloride (4.0 g, 26.1 mmol). The reaction mixture was agitated for approximately 16 hours. The reaction mixture was then made alkaline by the addition of sodium bicarbonate. The reaction mixture was then extracted with hexane, washed with a saturated sodium bicarbonate solution, dried over MgSO$_4$ and evaporated. The product was purified by recrystallization in hexane and cooled with a mixture of dry ice and acetone to give the title compound, 1-chloropyrrolo[1,2-a]pyrazine (71%), m.p. 56°-57° C.

PREPARATION 21

1-benzyloxypyrrolo[1,2-a]pyrazine (A compound of formula (DD))

To a solution of sodium hydride in anhydrous dimethylformamide was added benzyl alcohol (0.64 g, 5.9 mmol). The reaction mixture was stirred for 15 minutes. 1-chloropyrrolo[1,2-a]pyrazine (0.90 g, 5.9 mmol) in anhydrous dimethylformamide was then rapidly added to the reaction mixture. The reaction mixture was then heated to 100° C. for approximately 30 minutes. It was then allowed to cool to room temperature and water was added. The product was then extracted with methylene chloride, washed with a saturated sodium chloride solution, dried over MgSO$_4$ and evaporated. The product was then purified by recrystallization in ether-hexane to give the title compound, 1-benzyloxypyrrolo[1,2-a]pyrazine (75%), m.p. 62°-63° C.

B. In a similar manner, but replacing benzyl alcohol with benzyl thiol, the following compound was made: 1-benzylthiopyrrole[1,2-a]pyrazine, m.p. 71°-72° C.

PREPARATION 22

1-(2-hydroxy-2-phenylethyl)pyrrolo[1,2-a]pyrazine (A compound of formula (GG))

A solution of 1-methylpyrrolo[1,2-a]pyrazine (7.94 g, 60 mmol) in anhydrous THF was cooled to −78° C. A 2.3M solution of n-butyllithium (4.99 g, 78 mmoles) in hexane was then added to the reaction mixture. The temperature of the reaction mixture was allowed to rise to 0° C. The reaction mixture was then stirred for 10 minutes and then recooled to −78° C. Benzaldehyde (7.93 ml, 8.3 g, 78 mmol) was then added to the reaction mixture. The temperature of the reaction mixture was then allowed to rise to 20° C. and then the reaction mixture was stirred for 1.5 hours. The reaction mixture was then poured into a saturated solution of NH$_4$Cl (500 ml), extracted with ethyl acetate (4×400 ml), dried over Na$_2$SO$_4$ and concentrated. The resulting product was then purified by column chromatography [silica gel, 500 g, CH$_2$Cl$_2$-MeOH (98:2)] to afford 10 g (70%) of the title compound, 1-(2-hydroxy-2-phenylethyl)pyrrolo[1,2-a]pyrazine, m.p. 70°-72° C.

PREPARATION 23

1-(2-phenylethenyl)pyrrolo[1,2-a]pyrazine (A compound of formula (HH))

1-(2-hydroxy-2-phenylethyl)pyrrolo[1,2-a]pyrazine (10 g, 42 mmol) and sulfuric acid (4.11 g, 42 mmol) were dissolved in toluene (100 mL). To this solution was added water (15 mL). The reaction mixture was heated to reflux for 48 hours. The reaction mixture was cooled to room temperature, poured into water (200 mL), and neutralized with concentrated solution of ammonium hydroxide (pH 12). The organic phase was then separated and the aqueous phase extracted with ethyl acetate (3×200 mL). The combined extracts were dried over Na$_2$SO$_4$ and concentrated. The resulting product was then purified by column chromatography [silica gel, 600 g, hexane:ethyl acetate (8:2)] to afford 6.9 g (75%) of the title compound, 1-(2-phenylethenyl)pyrrolo[1,2-a]pyrazine, as yellow crystals, m.p. 95°-97° C.

PREPARATION 24

1-(2-phenylethyl)-7-ethylpyrrolo[1,2-a]pyrazine (A compound of formula (F))

A. A solution of 1-(2-phenylethyl)-7-bromopyrrolo[1,2-a]pyrazine (3 g, 9.96 mmol) in THF (25 mL) was placed in an apparatus for extreme anhydrous conditions. The solution was cooled to −78° C. and n-butyllithium (10.9 mmol, 416 mL of a 2.4M solution in cyclohexane) was added. The reaction was stirred at −78° C. for 10 minutes and ethyl iodide (31 g, 199 mmol, 15 mL, 20 eq.) was added. The reaction was poured onto a saturated solution of ammonium chloride (150 mL), then extracted with ether (2×100 mL). The combined extracts were washed with a saturated solution of sodium bicarbonate (100 mL), NaCl (100 mL), dried over MgSO$_4$ and concentrated. The product was purified by column chromatography [silica gel, 300 g, hexane:ethyl acetate (90:10)] to obtain 1.1 g (44%) of the title compound, 1-(2-phenylethyl)-7-ethylpyrrolo[1,2-a]pyrazine, as an oil, ms 250 (M+).

B. In a similar manner, but replacing 1-(2-phenylethyl)-7-bromopyrrolo[1,2-a]pyrazine with other halopyrrolo[1,2-a]pyrazines and replacing ethyl iodide with other lower alkyl halides or lower alkyldisulfides, the following compounds were made:

1-(2-phenylethyl)-7-methylpyrrolo[1,2-a]pyrazine, ms 236 (M+);

1-(2-phenylethyl)-8-methylpyrrolo[1,2-a]pyrazine, m.p. 63°-65° C.;

1-(2-phenylethyl)-7-methylthiopyrrolo[1,2-a]pyrazine, ms 268 (M+);

1-(2-phenylethyl)-7-ethylthiopyrrolo[1,2-a]pyrazine;

1-(2-phenylethyl)-8-methylthiopyrrolo[1,2-a]pyrazine, ms 268 (M+);

1-(2-phenylethyl)-8-ethylthiopyrrolo[1,2-a]pyrazine; NMR: (CDCl$_3$) 1.31(t, J=7.5 Hz, 3H, CH$_2$CH$_3$), 2.85(q, J=7.5 Hz, 2H, CH$_2$, CH$_3$), 3.03-3.33(m, 2H), 3.61-3.91(m, 2H), 7.90(d, J=3.10 Hz, 1H, pyrrole), 7.21-7.81(m, 8H, phenyl, pyrrole, pyrazine);

1-(2-phenylethyl)-8-n-propylthiopyrrolo[1,2-a]pyrazine, ms 310 (M+); and 1-(2-phenylethyl)-8-n-butylthiopyrrolo[1,2-a]pyrazine, ms 310 (M+).

PREPARATION 25

1-(2-phenylethyl)-6,8-dibromopyrrolo[1,2-a]pyrazine (A compound of formula (F))

A. A solution of 1-(2-phenylethyl)pyrrolo[1,2-a]pyrazine (5 g, 225 mmol) in anhydrous ethanol (100 mL), was cooled to −20° C. and $Br_2$ (7.2 g, 450 mmol), 2.5 mL) was added dropwise. After 5 minutes, the solution was made basic (pH 9) with a saturated solution of sodium carbonate. The reaction was poured onto water (200 mL) and extracted with ethyl acetate (2×150 mL). The combined organic extracts were dried, first with $Na_2SO_4$, then with $MgSO_4$, and concentrated and the residue purified by column chromatography [silica gel, 150 g, hexane-ethyl acetate (80:20)] to give 7 g (84%) of the title compound, 1-(2-phenylethyl)-6,8-dibromopyrrolo[1,2-a]pyrazine, m.p. 75°–76° C.

B. In a similar manner, but replacing 1-(2-phenylethyl)pyrrolo[1,2-a]pyrazine with 1-(2-phenylethyl)-7-methylpyrrolo[1,2-a]pyrazine, the following compound was made:

1-(2-phenylethyl)-6,8-dibromo-7-methylpyrrolo[1,2-a]pyrazine, m.p. 92°–93° C.

C. In a similar manner, but replacing 1-(2-phenylethyl)pyrrolo[1,2-a]pyrazine with other appropriately substituted pyrrolo[1,2-a]pyrazines, the following compounds are made:

1-(2-(4-methoxyphenyl)ethyl)-6,8-dibromopyrrolo[1,2-a]pyrazine;
1-(2-(4-chlorophenyl)ethyl)-6,8-dibromopyrrolo[1,2-a]pyrazine;
1-(2-(2-ethylphenyl)ethyl)-6,8-dibromopyrrolo[1,2-a]pyrazine;
1-(2-(3-methylthiophenyl)ethyl-6,8-dibromopyrrolo[1,2-a]pyrazine;
1-(2-(4-n-butylthiophenyl)ethyl-6,8-dibromopyrrolo[1,2-a]pyrazine; and
1-(3-phenylpropyl)-6,8-dibromopyrrolo[1,2-a]pyrazine.

PREPARATION 26

1-(2-phenylethyl)-8-ethylpyrrolo[1,2-a]pyrazine (Compounds of formulae (F), (S) or (EE))

A. A solution of 1-(2-phenylethyl)-8-bromopyrrolo[1,2-a]pyrazine (6 g, 19.9 mmol) in anhydrous THF (200 mL), was cooled to −78° C., and n-butyllithium (19.9 mmol, 12.4 mL of a solution 1.6M in cyclohexane) was added. The reaction was stirred at −78° C. for 5 minutes and ethyl iodide (18.6 g, 120 mmol, 10 mL) was added. The reaction mixture was then rapidly warmed to room temperature and stirred for 3 hours. The mixture was poured onto a saturated solution of ammonium chloride (100 mL). The phases were separated and the aqueous phase was extracted with ether (2×100 mL). The combined extracts were washed with a saturated solution of sodium bicarbonate (100 mL) and then water. The combined extracts were then dried over $MgSO_4$, concentrated, and purified by column chromatography [silica gel, 1 kg, hexane-ether (95:5)] to provide 1.83 g (36%) of the title compound 1-(2-phenylethyl)-8-ethylpyrrolo[1,2-a]pyrazine, as an oil, NMR: ($CDCl_3$) 1.35(t, 3H, J=6.5 Hz); 2.90–3.50(m, 6H); 6.60–6.71(m, 1H, H-7 pyrrole); 7.20–7.48(m, 7H, phenyl and H-6 pyrrole and H-3 of pyrazine); 7.65(d, 1H, H-4 pyrazine, J=3.2 Hz).

B. In a similar manner, but replacing 1-(2-phenylethyl)-8-bromopyrrolo[1,2-a]pyrazine with other appropriately substituted 8-halopyrrolo[1,2-a]pyrazines and ethyl iodide with the appropriate lower alkyl halide, the following compounds were made:

1-(2-phenylethyl)-7-methyl-8-ethylpyrrolo[1,2-a]pyrazine, m.p. 61°–63° C.; and
1-(2-phenylethyl)-7,8-dimethylpyrrolo[1,2-a]pyrazine, ms 250 (M+).

C. In a similar manner, but replacing 1-(2-phenylethyl)-8-bromopyrrolo[1,2-a]pyrazine with other appropriately substituted 8-halopyrrolo[1,2-a]pyrazines and ethyl iodide with the appropriate lower alkyl halide, the following compounds are made:

1-(2-phenylethyl)-7-methyl-8-n-propylpyrrolo[1,2-a]pyrazine;
1-(2-phenylethyl)-7-methyl-8-n-propylpyrrolo[1,2-a]pyrazine;
1-(2-phenylethenyl)-7-methyl-8-n-propylpyrrolo[1,2-a]pyrazine;
1-(3-phenylpropyl)-7-methyl-8-ethylpyrrolo[1,2-a]pyrazine;
1-benzyloxy-7-methyl-8-n-propylpyrrolo[1,2-a]pyrazine; and
1-benzylthio-7-methyl-8-ethylpyrrolo[1,2-a]pyrazine.

PREPARATION 27

1-(2-phenylethyl)-6-bromopyrrolo[1,2-a]pyrazine (Compounds of formulae (F), (S), (EE) or (JJ))

A. A solution of 1-(2-phenylethyl)pyrrolo[1,2-a]pyrazine (1.5 g, 6.6 mmol) in dry ethyl alcohol (30 mL) was cooled to −78° C., and, with stirring, a cool solution (−78° C.) of bromine (1.05 g, 6.6 mmol, 034 mL, 1 eq.) in ethyl alcohol (10 mL) was added. The reaction temperature was brought up to −20° C. Stirring was continued for 1 hour. The reaction mixture was then poured over a 10% solution of NaOH (100 mL) and extracted with $CH_2Cl_2$ (2×100 mL). The combined extracts were dried over $MgSO_4$, concentrated, and the residue purified by column chromatography [silica gel, 200 g, hexane-ethyl acetate (80:20)] to give 649 mg (32%) of the title compound, 1-(2-phenylethyl)-6-bromopyrrolo[1,2-a]pyrazine, as a solid, m.p. 96°–97° C., together with 800 mg (32%) of 1-(2-phenylethyl)-6,8-dibromo-pyrrolo[1,2-a]pyrazine.

B. In a similar manner, but replacing 1-(2-phenylethyl)pyrrolo[1,2-a]pyrazine with other appropriately substituted pyrrolo[1,2-a]pyrazines the following compounds are made:

1-(2-phenylethenyl)-6-bromopyrrolo[1,2-a]pyrazine;
1-(3-phenylpropyl)-6-bromopyrrolow[1,2-a]pyrazine;
1-benzyloxy-6-bromo[1,2-a]pyrazine; and
1-benzylthio-6-bromopyrrolo[1,2-a]pyrazine.

PREPARATION 28

1-(2-phenylethyl)-6-bromo-8-chloropyrrolo[1,2-a]pyrazine (Compounds of formulae (F), (S) or (EE))

A solution of 1-(2-phenylethyl)-6-bromopyrrolo[1,2-a]pyrazine (432 mg, 1.44 mmol) in anhydrous $CH_2Cl_2$ (15 mL), was cooled to −78° C. and sulfuryl chloride (251 mg, 1.86 mmol, 0.15 mL, 1.3 eq.) was slowly added. The reaction temperature was allowed to rise to 0° C., and stirred for 2 hours. The reaction mixture was poured over ice-water (20 g in 20 mL of water) and extracted with $CH_2Cl_2$ (2×20 mL). The combined organic extracts were dried over $MgSO_4$, concentrated and the residue purified by column chromatography [silica gel, 30 g, hexane-ethyl acetate (80:20)] to give 460 mg (63%) of the title compound, 1-(2-phenylethyl)-6-bromo-8-chloropyrrolo[1,2-a]pyrazine, as a yellow solid, m.p. 103°–104° C.

EXAMPLE 1

Bis-[1-(2-phenylethyl)-6-aminopyrrolo[1,2-a]pyrazine]-malonate (Salts of compounds of formulae (Ia), (Ib), (Ic) or (Id) where $R^1$ is —NH$_2$)

A. To a solution of 1-(2-phenylethyl)pyrrolo[1,2-a]pyrazine (300 mg, 1.3 mmol) in THF (5 mL) was added dropwise n-butylnitrite (2.83 g, 3.84 mL, 25 eq.). The reaction was heated to reflux for 30 minutes. The solvent was evaporated and the resulting nitroso compound was quickly passed through a chromatography column [silica gel, 5 g, hexane-ethyl acetate, (1:1)]. The solvent was evaporated under reduced pressure and the residue was dissolved in 13 mL of ethanol, followed by the addition of SnCl$_2$.2H$_2$O (1.47 g, 5 eq.). The reaction mixture was stirred for 3 hours at room temperature. The ethanol was evaporated under reduced pressure and the residue treated with a cool 2M solution of NaOH until it was basic (pH 10). The mixture was extracted with CH$_2$Cl$_2$ (2×30 mL); the organic extracts were combined, dried over MgSO$_4$ and concentrated. The product was purified by column chromatography [silica gel, 20 g, MeOH:CH$_2$Cl$_2$:NH$_4$OH, (60:20:1)]. The free base was reacted with an ethereal solution of malonic acid (281 mg, 2.7 mmol, 2 eq.) to give 175 mg (48%) of the title compound, bis-[1-(2-phenylethyl)-6-aminopyrrolo[1,2-a]pyrazine]-malonate, m.p. 159°–160° C.

B. In a similar manner, but replacing 1-(2-phenylethyl)pyrrolo[1,2-a]-pyrazine with the appropriate 1-substituted-pyrrolo[1,2-a]pyrazine, the following 6-amino salts were made:
bis-[1-phenyl-6-aminopyrrolo[1,2-a]pyrazine]malonate, m.p. 180°–182° C.;
bis-[1-(4-methylphenyl)-6-aminopyrrolo[1,2-a]pyrazine]malonate, m.p. 164°–166° C.;
bis-[1-(4-chlorophenyl)-6-aminopyrrolo[1,2-a]pyrazine]malonate, m.p. 164°–166° C.;
bis-[1-(3-chlorophenyl)-6-aminopyrrolo[1,2-a]pyrazine]malonate, m.p. 182°–184° C.;
bis-[1-(2-phenylethyl)-6-amino-7-methyl-8-ethylpyrrolo[1,2-a]pyrazine]malonate, m.p. 158°–159° C.;
bis-[1-(2-phenylethyl)-6-amino-7-methyl-8-bromopyrrolo[1,2-a]pyrazine]malonate, m.p. 204°–205° C.;
bis-[1-(2-phenylethyl)-6-amino-7-bromopyrrolo[1,2-a]pyrazine]malonate, m.p. 156°–158° C.;
bis-[1-(2-phenylethyl)-6-amino-7-ethylpyrrolo[1,2-a]malonate, m.p. 152°–153° C.;
bis-[1-(2-phenylethyl)-6-amino-7-methylthiopyrrolo[1,2-a]pyrazine]malonate, m.p. 139°–141° C.;
bis-[1-(2-phenylethyl)-6-amino-7-methylpyrrolo[1,2-a]pyrazine]malonate, mp 160°–162° C.;
bis-[1-(2-phenylethyl)-6-amino-8-methylpyrrolo[1,2-a]pyrazine]malonate, m.p. 164°–166° C.;
bis-[1-(2-phenylethyl)-6-amino-8-ethylpyrrolo[1,2-a]pyrazine]malonate, m.p. 166°–167° C.;
bis-[1-(2-phenylethyl)-6-amino-8-chloropyrrolo[1,2-a]pyrazine]malonate, m.p. 159°–160° C.;
bis-[1-(2-phenylethyl)-6-amino-8-ethylthiopyrrolo[1,2-a]pyrazine]malonate, m.p. 170°–175° C.;
bis-[1-phenethyl-6-amino-8-methylthiopyrrolo[1,2-a]pyrazine]malonate, m.p. 170°–179° C.;
bis-[1-(2-phenylethyl)-6-amino-7-chloropyrrolo[1,2-a]pyrazine]malonate, m.p. 177°–179° C.;
bis-[1-(2-phenylethyl)-6-amino-8-bromopyrrolo[1,2-a]pyrazine]malonate, m.p. 168°–169° C.; and
bis-[1-(2-phenylethenyl)-6-aminopyrrolo[1,2-a]pyrazine]bromohydrate, m.p. >300° C.

C. In a similar manner, but replacing 1-(2-phenylethyl)pyrrolo[1,2-a]-pyrazine with the appropriate 1-substituted-pyrrolo[1,2-a]pyrazine, the following 6-amino salts are made:
bis-[1-(2-(4-methoxyphenyl)ethyl)-6-amino-7-methyl-8-ethylpyrrolo[1,2-a]pyrazine]malonate,
bis-[1-(4-methoxyphenylmethyl)-6-amino-7-methyl-8-ethylpyrrolo[1,2-a]pyrazine]malonate,
bis-[1-(2-(3-methylphenyl)ethyl)-6-amino-7-methyl-8-bromopyrrolo[1,2-a]pyrazine]malonate,
bis-[1-(2-(2-chlorophenyl)ethyl)-6-amino-7-bromopyrrolo[1,2-a]pyrazine]malonate,
bis-[1-(2-(4-methylthiophenyl)ethyl)-6-amino-7-ethylpyrrolo[1,2-a]malonate;
bis-[1-(2-(3-n-butylphenyl)ethyl)-6-amino-7-methylthiopyrrolo[1,2-a]pyrazine]malonate;
bis-[1-(2-(3-n-butylphenyl)ethenyl)-6-amino-7-methylthiopyrrolo[1,2-a]pyrazine]malonate;
bis-[1-benzyloxy-6-amino-7-methylthiopyrrolo[1,2-a]pyrazine]malonate; and
bis-[1-benzylthio-6-amino-7-methylthiopyrrolo[1,2-a]pyrazine]malonate.

EXAMPLE 2

1-(2-phenylethyl)-6-N-methylaminopyrrolo[1,2-a]pyrazine (A compound of formulae (Ia), (Ib), (Ic) or (Id) where $R^1$ is —NHR$^5$)

A. To a solution of 1-(2-phenylethyl)-6-aminopyrrolo[1,2-a]pyrazine (the free amine of the salt) (1.30 g, 5.48 mmol) in acetic acid (32 mL), was added paraformadehyde (1.65 g). To the reaction mixture was then added cyanoborohydride (1.65 g, 26.25 mmol) in very small portions. The reaction mixture is then stirred for 30 minutes at room temperature. The reaction mixture was then cooled to −10° C. and poured into a 5% solution of NaOH (50 mL). The aqueous solution was then extracted with ethyl acetate (2×100 ml). The combined extracts were dried over MgSO$_4$, concentrated and purified by column chromatography (silica gel, 90 g, ethyl acetate) to give 1.25 g (50%) of the title compound,
1-(2-phenylethyl)-6-N-methylaminopyrrolo[1,2-a]pyrazine,
together with the starting material, ms (low resolution) 251 (M+). The malonate salt of the title compound had a melting point of 145°–146° C. (ether).

B. In a similar manner, but replacing 1-(2-phenylethyl)-6-aminopyrrolo[1,2-a]pyrazine with the appropriate 6-aminopyrrolo[1,2-a]pyrazine, the following compounds are made:
1-(2-phenylethenyl)-6-N-methylaminopyrrolo[1,2-a]pyrazine;
1-(3-ethylphenyl)-6-N-methylaminomethylpyrrolo[1,2-a]pyrazine;
1-(3-n-butylphenyl)-6-N-methylaminopyrrolo[1,2-a]pyrazine;
1-(3-propylthiophenyl)-6-N-methylaminopyrrolo[1,2-a]pyrazine;

1-(4-butoxyphenyl)-6-N-methylaminopyrrolo[1,2-a]pyrazine;

1-(2-chlorophenyl)-6-N-methylaminopyrrolo[1,2-a]pyrazine;

1-(2-(4-ethylthiophenyl)ethyl)-6-N-methylamino-7-methyl-8-ethylpyrrolo[1,2-a]pyrazine;

1-(4-methoxybenzyl)oxy-6-N-methylaminopyrrolo[1,2-a]pyrazine; and 1-(3-methylbenzyl)thio-6-N-methylaminopyrrolo[1,2-a]pyrazine.

EXAMPLE 3

1-(2-phenylethyl)-6-(N,N-dimethylamino)methylpyrrolo[1,2-a]pyrazine (Compounds of formula (LL))

A. A 500 mL round bottom flask was half-filled with paraformaldehyde (~200 g) and then connected by means of a rubber hose to an acetone-dry ice trap. The trap was fitted with a 100 mL round bottom flask that contained dry dimethylamine hydrochloride (880 mg, 18 mmol. 1.2 eq. with respect to 1-(2-phenylethyl)pyrrolo[1,2-a]pyrazine). The flask containing the dimethylamine hydrochloride was then cooled to −78° C. and the flask containing the paraformaldehyde was heated between 180°-200° C. until an excess of paraformaldehyde had been distilled. The reaction mixture was then allowed to warm to room temperature. The solid mixture was cooled again to −20° C. and a solution of 1-(2-phenylethyl)pyrrolo[1,2-a]pyrazine (2 g., 9 mmol) in 20 mL of dry $CH_3CN$ was added. The reaction mixture was allowed to reach room temperature and left stirring at this temperature for 8 hours. A solution of NaOH (5M, 40 mL) was then added. The resulting solution was extracted with ethyl acetate (3×30 mL). The organic extracts were extracted with a solution of HCl (0.1M, 50 mL). The aqueous acid phase was then separated, neutralized with a solution of NaOH (2M, 50 mL) and extracted with ethyl acetate (2×50 mL). The organic extracts were combined, dried over $MgSO_4$ and evaporated to give 1.8 g (73%) of the title compound, 1-(2-phenylethyl)-6-(N,N-dimethylamino)methylpyrrolo[1,2-a]pyrazine, as an oil, ms 279 ($M^+$).

B. In a similar manner, but replacing 1-(2-phenylethyl)pyrrolo[1,2-a]pyrazine with other appropriately substituted pyrrolo[1,2-a]pyrazines, the following compounds were made:

1-(2-phenylethyl)-6-(N,N-dimethylamino)methyl-7-bromopyrrolo[1,2-a]pyrazine, m.p. 73°-74° C.;

1-(2-phenylethyl)-6-(N,N-dimethylamino)methyl-7-methylthiopyrrolo[1,2-a]pyrazine, as an oil, ms 225 ($M^+$);

1-(2-phenylethyl)-6-(N,N-dimethylamino)methyl-7-ethylthiopyrrolo[1,2-a]pyrazine, as an oil, ms 295 ($M^+$);

1-(2-phenylethyl)-6-(N,N-dimethylamino)methyl-8-n-propylthiopyrrolo[1,2-a]pyrazine, as a liquid, ms 353 ($M^+$);

1-(2-phenylethyl)-6-(N,N-dimethylamino)methyl-8-n-butylthiopyrrolo[1,2-a]pyrazine, as a liquid, ms 367 ($M^+$);

1-(2-phenylethyl)-6-(N,N-dimethylamino)methyl-7-methylpyrrolo[1,2-a]pyrazine, as an oil, NMR: ($CDCl_3$) 2.21(s, 6H); 281(s, 3H); 3.28(s, 4H); 3.60(s, 2H); 6.57(s, 1H, H-8 pyrrole); 7.20-7.40(m, 5H, phenyl); 7.47(d, 1H, H-3 pyrazine, J=5.1 Hz); 7.86(d, 1H, H-4 pyrazine, J=5.1 Hz);

1-(2-phenylethyl)-6-(N,N-dimethylamino)methyl-7-ethylpyrrolo[1,2-a]pyrazine, as an oil, ms 307 ($M^+$);

1-(2-phenylethyl)-6-(N,N-dimethylamino)methyl-8-ethylpyrrolo[1,2-a]pyrazine, as a slightly yellow oil, ms 307 ($M^+$);

1-(2-phenylethyl)-6-(N,N-dimethylamino)methyl-8-methylpyrrolo[1,2-a]pyrazine, ms 293 ($M^+$);

1-(2-phenylethyl)-6-(N,N-dimethylamino)methyl-7-chloropyrrolo[1,2-a]pyrazine, ms 313 ($M^+$);

1-(3-phenylpropyl)-6-(N,N-dimethylamino)methylpyrrolo[1,2-a]pyrazine, ms 293 ($M^+$);

1-(2-(4-methylphenyl)ethyl)-6-(N,N-dimethylamino)methylpyrrolo[1,2-a]pyrazine, ms 293 ($M^+$);

1-(2-(4-chlorophenyl)ethyl)-6-(N,N-dimethylamino)methylpyrrolo[1,2-a]pyrazine, as a slightly yellow oil, NMR: ($CDCl_3$) 2.20(s, 6H); 3.05-3.30(m, 4H); 3.68(s, 2H); 6.70(s, 2H); 7.15-7.35(m, 4H); 7.49(d, 1H, H-3 pyrazine, J=4.1 Hz); 7.95(d, 1H, H-4 pyrazine, J=4.1 Hz);

1-(2-(2-methoxyphenyl)ethyl)-6-(N,N-dimethylamino)methylpyrrolo[1,2-a]pyrazine, ms 309 ($M^+$);

1-phenyl-6-(N,N-dimethylamino)methylpyrrolo[1,2-a]pyrazine, ms 251 ($M^+$);

1-(4-methylphenyl)-6-(N,N-dimethylamino)methylpyrrolo[1,2-a]pyrazine, ms 265 ($M^+$);

1-(4-methylthiophenyl)-6-(N,N-dimethylamino)methylpyrrolo[1,2-a]pyrazine, m.p. 79°-81° C.;

1-(4-methoxyphenyl)-6-(N,N-dimethylamino)methylpyrrolo[1,2-a]pyrazine, ms 281 ($M^+$);

1-(4-chlorophenyl)-6-(N,N-dimethylamino)methylpyrrolo[1,2-a]pyrazine, ms 286 ($M^+$);

1-(2-(4-methylthio)phenyl)ethyl-6-(N,N-dimethylamino)methylpyrrolo[1,2-a]pyrazine, ms 325 ($M^+$);

1-(3-chlorophenyl)-6-(N,N-dimethylamino)methylpyrrolo[1,2-a]pyrazine, ms 285 ($M^+$);

1-(2-phenylethyl)-6-(N,N-dimethylamino)methyl-7-methyl-8-ethylpyrrolo[1,2-a]pyrazine, ms 321 ($M^+$);

1-(2-(4-chlorophenyl)ethyl)-6-(N,N-dimethyl)aminomethyl-7-chloropyrrolo[1,2-a]pyrazine, NMR: ($CDCl_3$) 2.23(s, 6H); 3.13(s, 4H); 3.66(s, $CH_2$); 6.66(s, 1H pyrrole); 7.20(s, 4H aryl); 7.53(d, 1H pyrazine); 7.90(d, 1H pyrazine);

1-benzyloxy-6-(N,N-dimethylamino)methylpyrrolo[1,2-a]pyrazine, ms 281 ($M^+$); and 1-benzylthio-6-(N,N-dimethylamino)methylpyrrolo[1,2-a]pyrazine, ms 297 ($M^+$).

C. In a similar manner, but replacing 1-(2-phenylethyl)pyrrolo[1,2-a]pyrazine with the appropriate substituted pyrrolo[1,2-a]pyrazine, the following compounds are made:

1-(3-ethylphenyl)-6-(N,N-dimethylamino)methylpyrrolo[1,2-a]pyrazine;

1-(3-n-butylphenyl)-6-(N,N-dimethylamino)methylpyrrolo[1,2-a]pyrazine;

1-(3-propylthiophenyl)-6-(N,N-dimethylamino)methylpyrrolo[1,2-a]pyrazine;

1-(4-butoxyphenyl)-6-(N,N-dimethylamino)methylpyrrolo[1,2-a]pyrazine;

1-(2-(2-chlorophenyl)ethenyl)-6-(N,N-dimethylamino)methylpyrrolo[1,2-a]pyrazine;

1-(2-chlorophenyl)-6-(N,N-dimethylamino)methylpyrrolo[1,2-a]pyrazine;

1-(2-(3-methylthio)phenyl)ethyl-6-(N,N-dimethylamino)methylpyrrolo[1,2-a]pyrazine;

1-(2-(3-propylthiophenyl)ethyl)-6-(N,N-dimethylamino)methylpyrrolo[1,2-a]pyrazine;

1-(2-(4-ethylthiophenyl)ethyl)-6-(N,N-dimethylamino)-methyl-7-methyl-8-ethylpyrrolo[1,2-a]pyrazine;

1-(4-methoxybenzyl)oxy-6-(N,N-dimethylamino)methylpyrrolo[1,2-a]pyrazine; and 1-(3-methylbenzyl)thio-6-(N,N-dimethylamino)methylpyrrolo[1,2-a]pyrazine.

D. Alternatively, compounds of formula (LL) were prepared as follows:

A solution of trifluoroacetic acid (29.6 g, 20 mL, 260 mmol) was cooled to −15° C., and bis-dimethylaminomethane (2.45 g, 24 mmol, 1.2 eq.) was slowly added (30 min.). Once the addition was finished 1-(4-phenylbutyl)pyrrolo[1,2-a]pyrazine (5 g, 20 mmol) was added, the temperature was raised to reflux. The reaction mixture was stirred for 8 hours, cooled, and poured over a 5M solution of NaOH (100 mL) and ice (100 g). The reaction mixture was then extracted with ethyl acetate (2×50 mL). The organic extracts were combined, washed with water (30 mL) and a saturated solution of NaCl (30 mL), dried over $MgSO_4$ and concentrated. The residue was purified by column chromatography [silica gel, 90 g, hexane-ethyl acetate (1:1)] to give 4.5 g (73%) of 1-(4-phenylbutyl)-6-(N,N-dimethylamino)methylpyrrolo[1,2-a]pyrazine as a dark green oil, ms 289 (M+).

E. In a similar manner, but replacing 1-(4-phenylbutyl)-pyrrolo[1,2-a]pyrazine with 1-(2-(4-methoxyphenyl)ethyl)pyrrolo[1,2-a]pyrazine, the following compound was made:

1-(2-(4-methoxyphenyl)ethyl)-6-(N,N-dimethylamino)-methylpyrrolo[1,2-a]pyrazine, NMR: ($CDCl_3$) 2.10-2.32(m, 6H); 3.00-3.37(m, 4H); 3.67(s,2H); 3.78(s, 3H); 6.72(s, 2H, H-7, H-8 pyrrole); 6.84(d, 2H, H-3', H-5' phenyl, J=8.9 Hz): 7.22(d, 2H, H-2', H-6' phenyl, J=8.9 Hz); 7.50(d, 1H, H-3 pyrazine, J=5.3 Hz); 7.94(d, 1H, H-4 pyrazine, J=5.3 Hz).

EXAMPLE 4

1-(2-phenylethyl)-6-cyanomethylpyrrolo[1,2-a]pyrazine (Compounds of formula (Ie))

A. To a solution of 1-(2-phenylethyl)-6-(N,N-dimethylamino)methylpyrrolo[1,2-a]pyrazine (1 g, 3.6 mmol) in 20 ml of dry MeOH, a solution of methyl iodide (4.6 g, 36 mmol, 2.2 mL, 10 eq.) in 5 mL of dry MeOH was added dropwise at 0° C. The reaction mixture was allowed to rise to room temperature and stirred at that temperature for 5 hours. The methanol was evaporated (avoiding heating). The solid residue was dissolved in acetonitrile (20 mL), and dry NaCN (1.1 g, 7.2 mmol, 2 eq.) was added. The reaction mixture was heated to reflux for 3 hours, allowed to cool and treated with 50 mL of a 1M solution of NaOH. The basic solution was extracted with ethyl acetate (2×50 mL), dried over $MgSO_4$ and evaporated. The residue was purified by column chromatography [silica gel, 40 g, hexane:ethyl acetate (8:2)] to give 0.68 g (69%) of the title compound, 1-(2-phenylethyl)-6-cyanomethylpyrrolo[1,2-a]pyrazine, m.p. 74°-75° C.

B. In a similar manner, but replacing 1-(2-phenylethyl)-6-(N,N-dimethylamino)methylpyrrolo[1,2-a]pyrazine with other appropriately substituted 6-(N,N-dimethylamino)methylpyrrolo[1,2-a]pyrazines, the following compounds were made:

1-(2-phenylethyl)-6-cyanomethyl-8-bromopyrrolo[1,2-a]pyrazine, m.p. 122°-123° C.;

1-(2-phenylethyl)-6-cyanomethyl-7-methylthiopyrrolo[1,2-a]pyrazine, ms 307 (M+);

1-(2-phenylethyl)-6-cyanomethyl-7-ethylthiopyrrolo[1,2-a]pyrazine, ms 321 (M+);

1-(2-phenylethyl)-6-cyanomethyl-7-methylpyrrolo[1,2-a]pyrazine, ms 275 (M+);

1-(2-phenylethyl)-6-cyanomethyl-7-methyl-8-bromopyrrolo[1,2-a]pyrazine, m.p. 142°-143° C.;

1-(2-phenylethyl)-6-cyanomethyl-7-ethylpyrrolo[1,2-a]pyrazine, ms 289 (M+);

1-(2-phenylethyl)-6-cyanomethyl-8-ethylpyrrolo[1,2-a]pyrazine, ms 289 (M+);

1-(2-phenylethyl)-6-cyanomethyl-8-methylpyrrolo[1,2-a]pyrazine, m.p. 59°-60° C.;

1-(2-phenylethyl)-6-cyanomethyl-7-chloropyrrolo[1,2-a]pyrazine, m.p. 108°-110° C.;

1-(3-phenylpropyl)-6-cyanomethylpyrrolo[1,2-a]pyrazine, ms 275 (M+);

1-(4-phenylbutyl)-6-cyanomethylpyrrolo[1,2-a]pyrazine, ms 307 (M+);

1-(2-(4-methylphenyl)ethyl)-6-cyanomethylpyrrolo[1,2-a]pyrazine, m.p. 101°-102° C.;

1-(2-(4-chlorophenyl)ethyl)-6-cyanomethylpyrrolo[1,2-a]pyrazine, m.p. 83°-84° C.;

1-(2-(4-chlorophenyl)ethyl)-6-cyanomethyl-7-chloropyrrolo[1,2-a]pyrazine, m.p. 152°-153° C.;

1-(2-(4-methoxyphenyl)ethyl)-6-cyanomethylpyrrolo[1,2-a]pyrazine, m.p. 85°-86° C.;

1-(2-(2-methoxyphenyl)ethyl)-6-cyanomethylpyrrolo[1,2-a]pyrazine, ms 291 (M+);

1-phenyl-6-cyanomethylpyrrolo[1,2-a]pyrazine, m.p. 123°-124° C.;

1-(4-methylphenyl)-6-cyanomethylpyrrolo[1,2-a]pyrazine, m.p. 116°-120° C.;

1-(4-methoxyphenyl)-6-cyanomethylpyrrolo[1,2-a]pyrazine, ms 263 (M+);

1-(4-methylthiophenyl)-6-cyanomethylpyrrolo[1,2-a]pyrazine, m.p. 110°-112° C.;

1-(4-chlorophenyl)-6-cyanomethylpyrrolo[1,2-a]pyrazine, m.p. 120°-122° C.;

1-(2-(4-methylthiophenyl)ethyl-6-cyanomethylpyrrolo[1,2-a]pyrazine, m.p. 85°-86° C.;

1-(3-chlorophenyl)-6-cyanomethylpyrrolo[1,2-a]pyrazine, m.p. 84°-86° C.;

1-(2-phenylethyl)-6-cyanomethyl-7-methyl-8-ethylpyrrolo[1,2-a]pyrazine, m.p. 83°-84° C.;

1-(2-phenylethyl)-6-cyanomethyl-7,8-dimethylpyrrolo[1,2-a]pyrazine, m.p. 135°-136° C.;

1-benzyloxy-6-cyanomethylpyrrolo[1,2-a]pyrazine, m.p. 81°-82° C.; and 1-benzylthio-6-cyanomethylpyrrolo[1,2-a]pyrazine, m.p. 94°-96° C.

C. In a similar manner, but replacing 1-(2-phenylethyl)-6-(N,N-dimethylamino)methylpyrrolo[1,2-a]pyrazine with the appropriate 6-(N,N-dimethylamino)methylpyrrolo[1,2-a]pyrazine, the following compounds are made:

1-(3-ethylphenyl)-6-cyanomethylpyrrolo[1,2-a]pyrazine;

1-(2-phenylethenyl)-6-cyanomethylpyrrolo[1,2-a]pyrazine;

1-(3-n-butylphenyl)-6-cyanomethylpyrrolo1,2-a]pyrazine;

1-(3-propylthiophenyl)-6-cyanomethylpyrrolo[1,2-a]pyrazine;

1-(4-butoxyphenyl)-6-cyanomethylpyrrolo[1,2-a]pyrazine;

1-(2-chlorophenyl)-6-cyanomethylpyrrolo[1,2-a]pyrazine;

1-(2-(3-methylthio)phenyl)ethyl-6-cyanomethylpyrrolo[1,2-a]pyrazine;

1-(2-(3-propylthiophenyl)ethyl)-6-cyanomethylpyrrolo[1,2-a]pyrazine;

1-(2-(4-ethylthiophenyl)ethyl)-6-cyanomethyl-7-methyl-8-ethylpyrrolo[1,2-a]pyrazine;

1-(4-methoxybenzyl)oxy-6-cyanomethylpyrrolo[1,2-a]pyrazine; and 1-(3-methylbenzyl)thio-6-cyanomethylpyrrolo[1,2-a]pyrazine.

EXAMPLE 5

1-(2-phenylethyl)-6-cyanomethyl-8-thiocyanopyrrolo[1,2-a]pyrazine (Compounds of formula (Ie))

A. A mixture of potassium thiocyanate (605 mg, 6.3 mmol), and dry methanol (5 mL) was cooled to −78° C. and bromine (245 mg, 1.53 mmol, 0.078 mL) in dry methanol (5 ml) was rapidly added. The mixture was stirred at −78° C. for 30 minutes, and added to a solution of 1-(2-phenylethyl)-6-cyanomethylpyrrolo[1,2-a]pyrazine (200 mg, 0.80 mmol) in dry methanol (10 mL). The reaction mixture temperature was allowed to rise to 0° C. and stirred at that temperature for 30 minutes. The reaction mixture was then poured into ice-water (100 g), neutralized with a saturated solution of sodium bicarbonate (100 mL) and then extracted with ethyl acetate (2×50 mL). The combined extracts were dried over MgSO$_4$, concentrated and the residue purified by column chromatography [silica gel, 20 g, hexane-ethyl acetate (60:40)] to give 128 mg (53%) of the title compound, 1-(2-phenylethyl)-6-cyanomethyl-8-thiocyanopyrrolo[1,2-a]pyrazine, m.p. 75°–76° C.

B. In a similar manner, but replacing 1-(2-phenylethyl)-6-cyanomethylpyrrolo[1,2-a]pyrazine with other appropriately substituted pyrrolo[1,2-a]pyrazines, the following compounds were made:

1-(2-phenylethyl)-6-thiocyanopyrrolo[1,2-a]pyrazine, NMR: (CDCl$_3$) 3.00–3.50(m, 8H), 6.74(d, J=4.5 Hz, 1H, pyrrole), 7.10–7.50(m, 6H, phenyl, pyrrole), 7.86(d, J=5.1 Hz, 1H, H-3, 8.10(d, J=5.1, 1H, H-4);

1-phenyl-6-thiocyanopyrrolo[1,2-a]pyrazine, m.p. 83°–85° C.;

1-(4-methoxyphenyl)-6-thiocyanopyrrolo[1,2-a]pyrazine, m.p. 121°–123° C.;

1-(4-methylphenyl)-6-cyanomethyl-8-thiocyanopyrrolo[1,2-a]pyrazine, m.p. 168°–169° C.;

1-(4-chlorophenyl)-6-cyanomethyl-8-thiocyanopyrrolo[1,2-a]pyrazine, ms 324 (M+);

1-(2-phenylethyl)-6-cyanomethyl-7-methylthio-8-thiocyanopyrrolo[1,2-a]pyrazine, ms 364 (M+);

1-(2-phenylethyl)-6-cyanomethyl-7-ethylthio-8-thiocyanopyrrolo[1,2-a]pyrazine, m.p. 114°–115° C.; and 1-(2-phenylethyl)-6-cyanomethyl-7-bromo-8-thiocyanopyrrolo[1,2-a]pyrazine, m.p. 174°–175° C.

EXAMPLE 6

1-(2-phenylethyl)-6-cyanomethyl-8-methylthiopyrrolo[1,2-a]pyrazine (Compounds of formula (Ie))

A. To a solution of 1-(2-phenylethyl)-6-cyanomethyl-8-thiocyanopyrrolo[1,2-a]-pyrazine (900 mg, 2.83 mmol) in a mixture of methanol (15 mL) and dichloromethane (15 mL), cooled to 0° C., was added finely pulverized KOH (475 mg, 8.33 mmol, 3 eq.). The reaction mixture was stirred for 15 minutes, and then methyl iodide (2.1 g, 14.4 mmol, 0.92 mL, 5 eq.) was added. The reaction mixture was then stirred for 3 hours at room temperature. The solvent was then evaporated, and the residue taken up in ether (50 mL), dried over MgSO$_4$, and evaporated. The residue was purified by column chromatography [silica gel, 25 g, ether] to give 550 mg (65%) of the title compound, 1-(2-phenylethyl)-6-cyanomethyl-8-methylthiopyrrolo[1,2-a]pyrazine, ms 307 (M+).

B. In a similar manner, but replacing 1-(2-phenylethyl)-6-cyanomethyl-8-thiocyanopyrrolo[1,2-a]pyrazine with other appropriately substituted 8-thiocyanopyrrolo[1,2-a]pyrazines and replacing methyl iodide with other lower alkyl iodides, the following compounds were made:

1-(2-phenylethyl)-6-cyanomethyl-8-ethylthiopyrrolo[1,2-a]pyrazine, ms 321 (M+);

1-(2-phenylethyl)-6-cyanomethyl-8-(n-propylthio)pyrrolo[1,2-a]pyrazine, ms 335 (M+);

1-(2-phenylethyl)-6-cyanomethyl-8-(n-butylthio)pyrrolo[1,2-a]pyrazine, ms 349 (M+);

1-(2-phenylethyl)-6-cyanomethyl-8-(n-hexylthio)pyrrolo[1,2-a]pyrazine, ms 337 (M+);

1-(2-phenylethyl)-6-cyanomethyl-7,8-diethylthiopyrrolo[1,2-a]pyrazine, ms 381 (M+);

1-(4-methylphenyl)-6-cyanomethyl-8-ethylthiopyrrolo[1,2-a]pyrazine, ms 307 (M+);

1-(4-chlorophenyl)-6-cyanomethyl-8-methylthiopyrrolo[1,2-a]pyrazine, ms 313 (M+); and 1-(2-phenylethyl)-6-cyanomethyl-7-bromo-8-(n-propylthio)pyrrolo[1,2-a]pyrazine, ms 413 (M+).

C. In a similar manner, but replacing the lower alkyl iodide with n-hexylmethanesulfonate, the following compound was made:

1-(2-phenylethyl)-6-cyanomethyl-7-bromo-8-(n-hexylthio)pyrrolo[1,2-a]pyrazine, ms 455 (M+).

D. In a similar manner, but replacing 1-(2-phenylethyl)-6-cyanomethyl-8-thiocyanopyrrolo[1,2-a]pyrazine with other appropriately substituted 8-thiocyanopyrrolo[1,2-a]pyrazines and replacing methyl iodide with other lower alkyl iodides, the following compounds are made:

1-phenylmethyl-6-cyanomethyl-7,8-diethylthiopyrrolo[1,2-a]pyrazine;

1-(2-(4-methylphenyl)ethenyl-6-cyanomethyl-8-ethylthiopyrrolo[1,2-a]pyrazine;

1-benzyloxy-6-cyanomethyl-8-methylthiopyrrolo[1,2-a]pyrazine; and 1-benzylthio-6-cyanomethyl-7-bromo-8-(n-propylthio)-pyrrolo[1,2-a]pyrazine.

EXAMPLE 7

1-(2-phenylethyl)-6-cyanomethyl-8-bromopyrrolo[1,2-a]pyrazine (Compounds of formula (Ie))

A. A solution of 1-(2-phenylethyl)-6-cyanomethylpyrrolo[1,2-a]pyrazine (94 mg, 0.36 mmol) in anhydrous THF (5 mL) was cooled to −78° C., and N-bromosuccinimide (64 mg, 0.36 mmol) in anhydrous THF (5 mL) was added. The temperature was allowed to rise to room temperature and the reaction mixture was stirred for 2 hours. The reaction mixture was poured over a 10% solution of NaOH (10 mL), then it was extracted with ethyl acetate (2×20 mL). The combined extracts were washed with a saturated solution of NaCl (20 mL), dried over MgSO₄, concentrated and purified by column chromatography [silica gel, 15 g, ether], to give 89 mg (73%) of the title compound,
1-(2-phenylethyl)-6-cyanomethyl-8-bromopyrrolo[1,2-a]pyrazine, as a dark yellow solid, m.p. 85°–86° C.

B. In a similar manner, but replacing 1-(2-phenylethyl)-6-cyanomethylpyrrolo[1,2-a]pyrazine with other appropriately substituted 6-cyanomethylpyrrolo[1,2-a]pyrazines, the following compounds were made:
1-(4-methylphenyl)-6-cyanomethyl-8-bromopyrrolo[1,2-a]pyrazine, m.p. 180°–181° C.;
1-(4-chlorophenyl)-6-cyanomethyl-8-bromopyrrolo[1,2-a]pyrazine, m.p. 140°–141° C.; and
1-(2-phenylethyl)-6-cyanomethyl-7,8-dibromopyrrolo[1,2-a]pyrazine, m.p. 160°–161° C.

EXAMPLE 8

1-(2-phenylethyl)-6-cyanomethyl-8-chloropyrrolo[1,2-a]pyrazine (Compounds of formula (Ie))

A. A solution of 1-(2-phenylethyl)-6-cyanomethylpyrrolo[1,2-a]pyrazine (700 mg, 2.7 mmol) in dry dichloromethane (15 mL) was cooled to −78° C. and sulfuryl chloride (540 mg, 4 mmol, 0.32 mL) was added dropwise. The reaction temperature was raised to 0° C. and stirred for 1 hour. The reaction mixture was then poured onto a 10% solution of sodium bicarbonate (40 mL), and extracted with $CH_2Cl_2$ (2 × 30 mL). The combined extracts were dried over MgSO₄ and evaporated. The residue product was purified by column chromatography [silica gel, 60 g, hexane-ether (1:1)] to give 403 mg (51%) of the title compound,
1-(2-phenylethyl)-6-cyanomethyl-8-chloropyrrolo[1,2-a]pyrazine, as a solid, m.p. 89°–90° C.

B. In a similar manner, but replacing 1-(2-phenylethyl)-6-cyanomethylpyrrolo[1,2-a]pyrazine with the appropriately substituted pyrrolo[1,2-a]pyrazine, the following compounds were made:
1-(2-(4-methylphenyl)ethyl)-6-cyanomethyl-8-chloropyrrolo[1,2-a]pyrazine, m.p. 136°–137° C.;
1-(2-(4-chlorophenyl)ethyl)-6-cyanomethyl-7,8-dichloropyrrolo[1,2-a]pyrazine, m.p. 145°–146° C.;
1-phenyl-6-cyanomethyl-8-chloropyrrolo[1,2-a]pyrazine, m.p. 213°–214° C.;
1-(4-methylphenyl)-6-cyanomethyl-8-chloropyrrolo[1,2-a]pyrazine, m.p. 140°–141° C.;
1-(4-chlorophenyl)-6-cyanomethyl-8-chloropyrrolo[1,2-a]pyrazine, m.p. 154°–155° C.;
1-(2-phenylethyl)-6-cyanomethyl-7,8-dichloropyrrolo[1,2-a]pyrazine, m.p. 129°–130° C.; and
1-(2-phenylethyl)-6-cyanomethyl-7-bromo-8-chloropyrrolo[1,2-a]pyrazine, m.p. 160°–161° C.

EXAMPLE 9

1-(4-methylsulphonylphenyl)-6-cyanomethylpyrrolo[1,2-a]pyrazine (Compounds of formula (Ie))

A. A solution of 1-(4-methylthiophenyl)-6-cyanomethylpyrrolo[1,2-a]pyrazine (300 mg, 1.1 mmol) in dry $CH_2Cl_2$ (25 mL) was cooled to 0° C. and m-chloroperbenzoic acid (463 mg, 2.75 mmol, 2.5 eq.) in dry $CH_2Cl_2$ (5 mL) was added dropwise. The reaction mixture was stirred at room temperature for 3 hours, then made basic (pH 9) with a saturated solution of sodium carbonate. The reaction mixture was then extracted with $CH_2Cl_2$ (2 × 50 mL). The organic extracts were combined, washed with water (100 ml), dried over MgSO₄ and evaporated. The residue was purified by column chromatography [silica gel, 40 g, hexane-ethyl acetate (3:7)], to give 205 mg (60%) of the title compound,
1-(4-methylsulphonylphenyl)-6-cyanomethylpyrrolo[1,2-a]pyrazine, as a yellow solid, m.p. 188°–190° C.

B. In a similar manner, but replacing 1-(4-methylthiophenyl)-6-cyanomethylpyrrolo[1,2-a]pyrazine with 1-(2-(4-methylthiophenyl)ethyl)-6-cyanomethylpyrrolo[1,2-a]pyrazine, the following compound was made:
1-(2-(4-methylsulfonylphenyl)ethyl)-6-cyanomethylpyrrolo[1,2-a]pyrazine, ms 339 (M+).

C. In a similar manner, but replacing 1-(4-methylthiophenyl)-6-cyanomethylpyrrolo[1,2-a]pyrazine with the appropriate lower alkylthio-substituted, 6-cyanomethylpyrrolo[1,2-a]pyrazine or 6-aminopyrrolo[1,2-a]pyrazine, the following compounds are made:
1-(2-(4-n-butylsulfonylphenyl)ethyl)-6-cyanomethylpyrrolo[1,2-a]pyrazine;
1-(2-(4-n-propylsulfonylphenyl)ethyl)-6-cyanomethylpyrrolo[1,2-a]pyrazine;
1-(2-(3-n-butylsulfonylphenyl)ethyl)-6-cyanomethylpyrrolo[1,2-a]pyrazine;
1-(2-(3-n-propylsulfonylphenyl)ethyl)-6-cyanomethylpyrrolo[1,2-a]pyrazine;
1-(2-(4-n-butylsulfonylphenyl)ethyl)-6-(N,N-dimethylamino)methylpyrrolo[1,2-a]pyrazine;
1-(2-(4-n-propylsulfonylphenyl)ethyl)-6-(N,N-dimethylamino)methylpyrrolo[1,2-a]pyrazine;
1-(2-(3-n-butylsulfonylphenyl)ethyl)-6-(N,N-dimethylamino)methylpyrrolo[1,2-a]pyrazine; and
1-(2-(3-n-propylsulfonylphenyl)ethyl)-6-(N,N-dimethylamino)methylpyrrolo[1,2-a]pyrazine.

EXAMPLE 10

1-(2-phenylethyl)-6-ethoxymethyl-7-ethylpyrrolo[1,2-a]pyrazine (Compounds of formula (If))

A solution of 1-(2-phenylethyl)-6-N,N-dimethylaminomethyl-7-ethylpyrrolo[1,2-a]pyrazine (293 mg, 0.97 mmol) in dry methanol was reacted with methyl iodide (1.37 g, 9.7 mmol, 10 eq.). The reaction mixture was allowed to stir at room temperature for 4 hours, then sodium ethoxide (5.0 eq.) was added to the reaction mixture. The reaction mixture was refluxed for 15 minutes. The solvents were then eliminated and the product extracted with ethyl acetate (2 × 50 mL). The combined organic extracts were dried over MgSO₄, concentrated and purified (silica gel, 25 g, ethyl acetate/hexane (20:80)) to give 260 mg (85%) of the title compound,
1-(2-phenylethyl)-6-ethoxymethyl-7-ethylpyrrolo[1,2-a]pyrazine, as a liquid, NMR: (CDCl₃) 1.29(t, J=8.5 Hz, 6H, 2 CH₃), 2.75(q, J=8.5 Hz, 2H, CH₂CH₃), 3.10–3.31(m, 4H), 3.48(q, J=8.5 Hz, CH₃CH₂O), 4.73(s, 2H, OCH₂pyrrole), 6.59(s, pyrrole), 7.10–7.41(m, 5H, phenyl), 7.5(d, J=5.8 Hz, 1H, H-3, pyrazine), 7.82(d, J=5.8 Hz, 1H, H-4, pyrazine).

EXAMPLE 11

(Conversion of acid addition salts of formula (I) to the corresponding free bases)

A. A malonate salt of a compound of formula (I), for example, bis-[1-(2-phenylethyl)-6-aminopyrrolo[1,2- a]pyrazine]malonate, suspended in ethyl acetate, is stirred with an excess of dilute aqueous potassium carbonate solution until the malonate salt is dissolved. The organic layer is then separated, washed twice with water, dried over magnesium sulfate and evaporated to yield
1-(2-phenylethyl)-6-aminopyrrolo[1,2-a]pyrazine.

B. In a similar manner, the acid addition salts of all other compounds of formula (I) may be converted to the corresponding compounds in free base form.

EXAMPLE 12

This example illustrates the preparation of a representative pharmaceutical formulation for oral administration containing a compound of formula (I), e.g., 1-(2-phenylethyl)-6-cyanomethyl-8-ethylthiopyrrolo[1,2-a]pyrazine.

| Ingredients | Quantity per tablet, mgs. |
|---|---|
| Compound of formula (I) | 200 |
| lactose, spray-dried | 148 |
| magnesium stearate | 2 |

The above ingredients are mixed and introduced into a hard-shell gelatin capsule.

Other compounds of formula (I), such as those prepared in accordance with Examples 1-11, can be used as the compound in the preparation of the orally administrable formulations of this example.

EXAMPLE 13

This example illustrates the preparation of a representative pharmaceutical formulation containing a compound of formula (I), e.g., 1-(2-phenylethyl)-6-cyanomethyl-7-methyl-8-ethylpyrrolo[1,2-a]pyrazine.

An injectable preparation buffered to a pH of 4 is prepared having the following composition:

| Ingredients | |
|---|---|
| Compound of formula (I) | 0.2 g |
| Sodium Acetate Buffer Solution (0.4 M) | 2.0 mL |
| HCl (1N) | q.s. to pH 4 |
| water (distilled, sterile) | q.s. to 20 mL |

Other compounds of formula (I), such as those prepared in accordance with Examples 1-11, can be used as the compound in the preparation of the injectable formulations of this example.

EXAMPLE 14

This example illustrates the preparation of a representative pharmaceutical formulation for topical application containing a compound of formula (I), e.g., 1-(2-phenylethyl)-6-cyanomethyl-8-n-propylthiopyrrolo[1,2-a]pyrazine.

| Ingredients | grams |
|---|---|
| Compound of formula (I) | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water q.s. to | 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of formula (I), such as those prepared in accordance with Examples 1-11, can be used as the compound in the preparation of the topical formulations of this example.

EXAMPLE 15

This example illustrates the preparation of a representative pharmaceutical formulation containing a compound of formula (I), e.g., 1-(2-phenylethyl)-6-cyanomethyl-8-n-butylthio-pyrrolo[1,2-a]pyrazine.

A suppository totalling 2.5 grams is prepared having the following composition:

Compound of formula (I): 500 mg witepsol H-15: balance
*triglycerides of saturated vegetable fatty acid; a product of Riches-Nelson, Inc., New York, N.Y.

Other compounds of formula (I), such as those prepared in accordance with Examples 1-11, can be used as the active compound in the preparation of the suppository formulations of this example.

EXAMPLE 16

(In vitro assay)

$H^+/K^+$-ATPase enzyme, isolated from porcine gastric mucosa, was obtained from the Cure Foundation in Los Angeles, Calif. Hydrolysis of p-nitrophenylphosphate by $H^+/K^+$-ATPase was assayed in 1.0 mL incubation medium (40 mM Tris-HCl, 6.0 mM $MgCl_2$, 20.0 mM KCl, 6.0 mM p-nitrophenylphosphate, pH 7.4). Compounds of formula (I) were dissolved in dimethyl sulfoxide and added in 10.0 μL aliquots. The compounds were pre-incubated with $H^+$-$K^+$-ATPase in 10.0 mM Tris acetate, pH 6.1, for 10 minutes before the addition of p-nitrophenylphosphate. After incubation at 37° C. for 5–10 minutes, the reaction was terminated with 0.1 mL of 1N NaOH. The reaction mixture was centrifuged briefly and absorbance of the supernatant was measured at 410 nm. Absorbances were converted to percent inhibition from control and $IC_{50}$ values were determined by an iterative curve fitting program (*J. Pharm. Exp. Ther.*, 1972, Vol. 177, p.13). Compounds were initially screened at $1 \times 10^{-4}$M, in triplicate. Compounds showing greater than 50% inhibition were then tested at concentrations ranging from $10^{-7}$M to $10^{-4}$M.

Compounds of formula (I) exhibited inhibition of $H^+/K^+$-ATPase activity when tested by this method.

EXAMPLE 17

(In vivo assay)

Adult male Sprague-Dawly rats were fasted overnight with water allowed ad libitum. Each animal was anesthetized with urethane (1.25 to 1.50 g/kg, ip). A tracheostomy was performed and a length of PE-240 polyethylene tubing placed in the trachea. The tube was secured in the trachea with a ligature of silk suture. A PE-50 polyethylene catheter was placed in a femoral vein and connected to a Sage model 355 syringe infusion pump. A mid-line abdominal incision was made and the stomach and duodenum located. A length of PE-240 polyethylene tubing was placed in the stomach via the esophagus. A cannula prepared by cutting off the tapered end of a 1.0 cc disposable pipette was placed in the stomach via the duodenum and secured in place by a silk ligature around the pylorus. The duodenal cannula was exteriorized through a stab wound in the side of the rat. The abdominal incision was closed using wound clips.

Following surgical preparation, distilled water, warmed to 37° C., was constantly infused into the stomach via the indwelling catheter at a maintenance rate of 0.5 mL/min. by a Haake-Buchler Multistaltic Pump. The gastric effluent was collected in 10 minutes (5 mL) aliquots throughout the experiment utilizing a Haake-Buchler L200 fraction collector situated so as to collect fractions from each individual rat. Each animal was infused with the secretagogue histamine diphosphate via the indwelling femoral catheter at a rate of 63 μg/kg/min. This infusion continued for 60 minutes or steady state secretion was obtained, after which each animal was dosed with a compound of formula (I) and an additional 120 minutes period of secretgogue infusion carried out. Following this each animal was dosed with omeprazole (1.0 mg/kg, i.v.) and then a third period of secretagogue infusion completed. At the end of the third infusion period each animal was euthanzied by barbiturate injection.

A 1.0 ml aliquot of each 10 min. collection period for each animal was titrated to pH 7.0 with 0.005N sodium hydroxide. A Fisher Computerized Automatic Titrator was used for all titrations. The milliequivalents of acid for each sample was recorded.

Several compounds of formula (I) exhibited the ability to inhibit gastric acid secretion in the histamine-stimulated rat when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of formula (I):

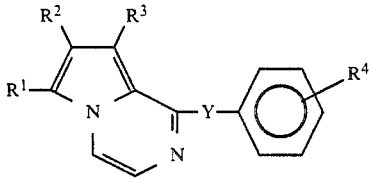
(I)

wherein
$R^1$ is thiocyano, —CH$_2$CN, —NH$_2$, —NHR$_5$, or —CH$_2$OR$^5$ where $R^5$ is lower alkyl;
$R^2$ is hydrogen, halo, lower alkyl, or lower alkylthio;
$R^3$ is hydrogen, halo, lower alkyl, lower alkylthio, or thiocyano;
$R^4$ is hydrogen, halo, lower alkyl, lower alkoxy, lower alkylthio, or lower alkylsulfonyl; and
Y is —O—CH$_2$—, —S—CH$_2$—, —CH=CH—, or —(CH$_2$)$_n$— where n is 0, 1, 2, 3 or 4;
or a pharmaceutically acceptable salt thereof.

2. A compound of claim 1 wherein $R^1$ is —CH$_2$CN or —NH$_2$.

3. A compound of claim 1 wherein $R^2$ is hydrogen, halo or lower alkyl.

4. A compound of claim 3 wherein $R^2$ is hydrogen, bromo or methyl.

5. A compound of claim 1 wherein $R^4$ is in the 4-position and is hydrogen, lower alkyl or halo.

6. A compound of claim 1 wherein Y is —(CH$_2$)$_n$— where n is 0 or 2.

7. A compound of claim 6 wherein $R^2$ is hydrogen, halo or lower alkyl.

8. A compound of claim 7 wherein $R^4$ is in the 4-position and is hydrogen, halo or lower alkyl.

9. A compound of claim 8 wherein $R^3$ is lower alkyl.

10. A compound of claim 9 wherein $R^1$ is —NH$_2$ and Y is —CH$_2$—CH$_2$—.

11. The compound of claim 10 wherein $R^2$ is hydrogen, $R^3$ is ethyl, and $R^4$ is hydrogen, namely, 1-(2-phenylethyl)-6-amino-8-ethylpyrrolo[1,2-a]pyrazine.

12. The compound of claim 10 wherein $R^2$ is methyl, $R^3$ is ethyl, and $R^4$ is hydrogen, namely, 1-(2-phenylethyl)-6-amino-7-methyl-8-ethylpyrrolo[1,2-a]pyrazine.

13. A compound of claim 9 wherein $R^1$ is —CH$_2$CN and Y is —CH$_2$—CH$_2$—.

14. The compound of claim 13 wherein $R^2$ is methyl, $R^3$ is ethyl, and $R^4$ is hydrogen, namely, 1-(2-phenylethyl)-6-cyanomethyl-7-methyl-8-ethylpyrrolo[1,2-a]pyrazine.

15. A compound of claim 8 wherein $R^3$ is lower alkylthio.

16. A compound of claim 15 wherein $R^1$ is —NH$_2$ and Y is —CH$_2$—CH$_2$—.

17. The compound of claim 16 wherein $R^2$ and $R^4$ are hydrogen, and $R^3$ is methylthio, namely, 1-(2-phenylethyl)-6-amino-8-methylthiopyrrolo[1,2-a]pyrazine.

18. A compound of claim 15 wherein $R^1$ is —CH$_2$CN and Y is —CH$_2$—CH$_2$—.

19. The compound of claim 18 wherein $R^2$ and $R^4$ are hydrogen, and $R^3$ is ethylthio, namely, 1-(2-phenylethyl)-6-cyanomethyl-8-ethylthiopyrrolo[1,2-a]pyrazine.

20. The compound of claim 18 wherein $R^2$ and $R^4$ are hydrogen, and $R^3$ is n-propylthio, namely, 1-(2-phenylethyl)-6-cyanomethyl-8-n-propylthiopyrrolo[1,2-a]pyrazine.

21. The compound of claim 18 wherein $R^2$ and $R^4$ are hydrogen, and $R^3$ is n-butylthio, namely, 1-(2-phenylethyl)-6-cyanomethyl-8-n-butylthiopyrrolo[1,2-a]pyrazine.

22. A compound of claim 8 wherein $R^3$ is halo.

23. A compound of claim 22 wherein $R^1$ is —NH$_2$ and Y is —CH$_2$—CH$_2$—.

24. The compound of claim 23 wherein $R^2$ is methyl, $R^3$ is bromo and $R^4$ is hydrogen, namely, 1-(2-phenylethyl)-6-amino-7-methyl-8-bromopyrrolo[1,2-a]pyrazine.

25. A compound of claim 22 wherein $R^1$ is —CH$_2$CN and Y is —CH$_2$—CH$_2$—.

26. The compound of claim 25 wherein $R^2$ is chloro, $R^3$ is chloro and $R^4$ is hydrogen, namely, 1-(2-phenylethyl)-6-cyanomethyl-7,8-dichloropyrrolo[1,2-a]pyrazine.

27. A compound of claim 8 wherein $R^3$ is thiocyano.

28. A compound of claim 27 wherein $R^1$ is —$CH_2CN$ and Y is —$CH_2$—$CH_2$—.

29. The compound of claim 28 wherein $R^2$ is hydrogen and $R^4$ is 4-methyl, namely, 1-(2-(4-methylphenyl)ethyl)-6-cyanomethyl-8-thiocyanopyrrolo[1,2-a]pyrazine.

30. The compound of claim 28 wherein $R^2$ is bromo and $R^4$ is hydrogen, namely, 1-(2-phenylethyl)-6-cyanomethyl-7-bromo-8-thiocyanopyrrolo[1,2-a]pyrazine.

31. A compound useful as an intermediate in the synthesis of compounds of formula (I) wherein $R^1$ is —$CH_2CN$ or —$CH_2OR^5$, wherein said compound is of the formula (LL):

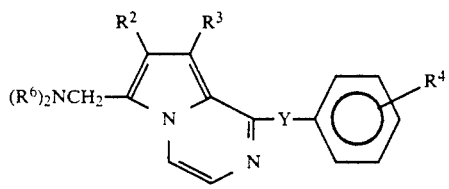

(LL)

wherein $R^2$ is hydrogen, halo, lower alkyl, or lower alkylthio;
$R^3$ is hydrogen, halo, lower alkyl, lower alkylthio, or thiocyano;
$R^4$ is hydrogen, halo, lower alkyl, lower alkoxy, lower alkylthio, or lower alkylsulfonyl;
$R^6$ is methyl; and
Y is —O—$CH_2$—, —S—$CH_2$—, —CH=CH—, or —$(CH_2)_n$— where n is 0, 1, 2, 3 or 4;

or a pharmaceutically acceptable salt thereof.

32. A pharmaceutical composition useful for treating a mammal having a disease-state characterized by excessive gastric acid secretion, which composition comprises a pharmaceutically acceptable excipient and a therapeutically effective amount of a compound of formula (I):

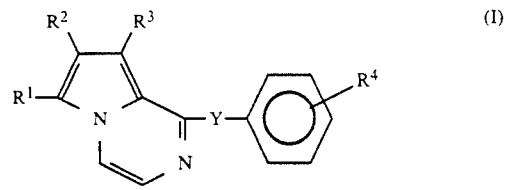

(I)

wherein $R^1$ is thiocyano, —$CH_2CN$, —$NH_2$, —$NHR_5$, or —$CH_2OR^5$ where $R^5$ is lower alkyl;
$R^2$ is hydrogen, halo, lower alkyl, or lower alkylthio;
$R^3$ is hydrogen, halo, lower alkyl, lower alkylthio, or thiocyano;
$R^4$ is hydrogen, halo, lower alkyl, lower alkoxy, lower alkylthio, or lower alkylsulfonyl; and
Y is —O—$CH_2$—, —S—$CH_2$—, —CH=CH—, or —$(CH_2)_n$— where n is 0, 1, 2, 3 or 4;

or a pharmaceutically acceptable salt thereof.

33. A method for treating a mammal having a disease-state characterized by excessive gastric acid secretion, which method comprises administering to a mammal in need thereof a therapeutically effective amount of a compound of formula (I):

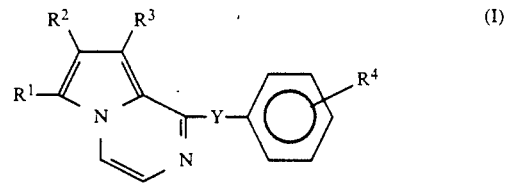

(I)

wherein $R^1$ is thiocyano, —$CH_2CN$, —$NH_2$, —$NHR_5$, or —$CH_2OR^5$ where $R^5$ is lower alkyl;
$R^2$ is hydrogen, halo, lower alkyl, or lower alkylthio;
$R^3$ is hydrogen, halo, lower alkyl, lower alkylthio, or thiocyano;
$R^4$ is hydrogen, halo, lower alkyl, lower alkoxy, lower alkylthio, or lower alkylsulfonyl; and
Y is —O—$CH_2$—, —S—$CH_2$—, —CH=CH—, or —$(CH_2)_n$— where n is 0, 1, 2, 3 or 4;

or a pharmaceutically acceptable salt thereof.

* * * * *